(12) United States Patent
Suzuki et al.

(10) Patent No.: US 8,419,628 B2
(45) Date of Patent: Apr. 16, 2013

(54) ENDOSCOPE SYSTEM AND ENDOSCOPIC IMAGE PROCESSING APPARATUS

(75) Inventors: Tatsuhiko Suzuki, Hino (JP); Masaru Sudo, Hachioji (JP); Kotaro Ogasawara, Tokyo (JP); Akihiko Mochida, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 146 days.

(21) Appl. No.: 12/797,938

(22) Filed: Jun. 10, 2010

(65) Prior Publication Data
US 2010/0331624 A1 Dec. 30, 2010

Related U.S. Application Data

(63) Continuation of application No. PCT/JP2009/067806, filed on Oct. 14, 2009.

(30) Foreign Application Priority Data

Oct. 17, 2008 (JP) ................................ 2008-268852
Oct. 17, 2008 (JP) ................................ 2008-268853

(51) Int. Cl.
*A61B 1/06* (2006.01)
*A61B 1/04* (2006.01)
*G06K 9/00* (2006.01)

(52) U.S. Cl.
USPC ............................ 600/160; 600/109; 382/128

(58) Field of Classification Search .................. 600/109, 600/160, 178, 180; 382/128; 348/68–70
See application file for complete search history.

(56) References Cited

U.S. PATENT DOCUMENTS 7,613,335 B2 * 11/2009 McLennan et al. ........... 382/128
7,898,699 B2 * 3/2011 Abe et al. ...................... 358/474
(Continued)

FOREIGN PATENT DOCUMENTS

EP 1 857 973 A1 11/2007
JP 07-178046 7/1995
(Continued)

OTHER PUBLICATIONS

International Search Report dated Dec. 28, 2009.
(Continued)

*Primary Examiner* — Philip R Smith
*Assistant Examiner* — William Chou
(74) *Attorney, Agent, or Firm* — Scully Scott Murphy & Presser, PC

(57) ABSTRACT

An endoscope system includes: an endoscope equipped with an insertion portion, and an image pickup unit disposed at a distal end portion of the insertion portion; an illumination unit detachably connected to the endoscope; an imaging mode input unit used to set an imaging mode of the endoscope to one of a normal-light mode and a special-light mode; a processing condition selection unit which selects a processing condition for a color correction process of an endoscopic image based on the imaging mode; and a processor detachably connected to the endoscope and equipped with an image processing unit which performs the color correction process, under the processing condition selected by the processing condition selection unit, with respect to each of hue regions partitioned by at least eight reference color axes including six reference color axes which divide a color space into R (red), M (magenta), B (blue), C (cyan), G (green), and Y (yellow) hue regions and at least two reference color axes established additionally based on the imaging mode.

12 Claims, 26 Drawing Sheets

U.S. PATENT DOCUMENTS

| | | | |
|---|---|---|---|
| 7,920,145 B2 * | 4/2011 | Yamano et al. | 345/589 |
| 8,027,533 B2 * | 9/2011 | Li et al. | 382/167 |
| 8,045,012 B2 * | 10/2011 | Miyanohara | 348/218.1 |
| 2005/0036668 A1 | 2/2005 | McLennan et al. | |
| 2006/0178565 A1 * | 8/2006 | Matsui et al. | 600/160 |
| 2007/0132839 A1 * | 6/2007 | Pang et al. | 348/65 |
| 2009/0052773 A1 | 2/2009 | Oohara | |

FOREIGN PATENT DOCUMENTS

| | | |
|---|---|---|
| JP | 08-238216 | 9/1996 |
| JP | 09-247701 | 9/1997 |
| JP | 2001-061160 | 3/2001 |
| JP | 2005-296200 | 10/2005 |
| JP | 2006-212335 | 8/2006 |
| JP | 2007-105290 | 4/2007 |
| JP | 2007-229054 | 9/2007 |
| JP | 2007-244681 | 9/2007 |
| JP | 2008-086605 | 4/2008 |
| JP | 2008-132321 | 6/2008 |
| WO | WO 2006/095496 A1 | 9/2006 |

OTHER PUBLICATIONS

Extended Supplementary European Search Report dated Jun. 21, 2012.

* cited by examiner

| RGB MAGNITUDE RELATIONSHIP | HUE REGION |
|---|---|
| R ≧ B ≧ G | REGION 1 |
| R ≧ G ≧ B | REGION 2 |
| G ≧ R ≧ B | REGION 3 |
| G ≧ B ≧ R | REGION 4 |
| B ≧ G ≧ R | REGION 5 |
| B ≧ R ≧ G | REGION 6 |

| RGB MAGNITUDE RELATIONSHIP | HUE REGION |
|---|---|
| $(2 \times B - G) > R$<br>$R \geq B \geq G$ | REGION 1A |
| $(2 \times B - G) \leq R$<br>$R \geq B \geq G$ | REGION 1B |
| $(2 \times G - B) \leq R$<br>$R \geq G \geq B$ | REGION 2A |
| $(2 \times G - B) > R$<br>$R \geq G \geq B$ | REGION 2B |
| $G \geq R \geq B$ | REGION 3 |
| $G \geq B \geq R$ | REGION 4 |
| $B \geq G \geq R$ | REGION 5 |
| $B \geq R \geq G$ | REGION 6 |

FIG.8A

MEMU　　　　　SCOPE – A

| Color axis | Sat. | Hue |
|---|---|---|
| M | 0 | 0 |
| R–M | –5 | +2 |
| R | +8 | +4 |
| R–Y | 0 | –2 |
| Y | +10 | 0 |
| G | 0 | 0 |
| C | 0 | 0 |
| B | 0 | 0 |

FIG.8B

MEMU　　　　　SCOPE – B

| Color axis | Sat. | Hue |
|---|---|---|
| M | 0 | 0 |
| R–M | +2 | 0 |
| R | +4 | 0 |
| R–Y | 0 | –2 |
| Y | +6 | 0 |
| G | 0 | 0 |
| C | 0 | 0 |
| B | 0 | 0 |

FIG.13A

MEMU      Xenon lamp

| Color axis | Sat. | Hue |
|---|---|---|
| M | 0 | 0 |
| R-M | 0 | 0 |
| R | 0 | 0 |
| R-Y | 0 | 0 |
| Y | 0 | 0 |
| G | 0 | 0 |
| C | 0 | 0 |
| B | 0 | 0 |

FIG.13B

MEMU      LED

| Color axis | Sat. | Hue |
|---|---|---|
| M | 0 | 0 |
| R-M | 0 | 0 |
| R | +2 | +1 |
| R-Y | 0 | 0 |
| Y | +3 | -2 |
| G | +1 | 0 |
| C | 0 | 0 |
| B | -4 | 0 |

FIG.14A

MEMU          stomach

| Color axis | Sat. | Hue |
|---|---|---|
| M | 0 | 0 |
| R-M | 0 | 0 |
| R | +8 | +4 |
| R-Y | 0 | 0 |
| Y | +10 | 0 |
| G | 0 | 0 |
| C | 0 | 0 |
| B | 0 | 0 |

FIG.14B

MEMU          otolaryngology

| Color axis | Sat. | Hue |
|---|---|---|
| M | 0 | 0 |
| R-M | -5 | +2 |
| R | -5 | +4 |
| R-Y | -5 | -2 |
| Y | 0 | 0 |
| G | 0 | 0 |
| C | 0 | 0 |
| B | 0 | 0 |

FIG.15A

MEMU　　　　　　　Normal

| Color axis | Sat. | Hue |
|---|---|---|
| M | 0 | 0 |
| R-M | -5 | +2 |
| R | +8 | +4 |
| R-Y | 0 | -2 |
| Y | +10 | 0 |
| G | 0 | 0 |
| C | 0 | 0 |
| B | 0 | 0 |

FIG.15B

MEMU　　　　　　　Bleeding scene

| Color axis | Sat. | Hue |
|---|---|---|
| M | 0 | 0 |
| R-M | -10 | +2 |
| R | -10 | +4 |
| R-Y | -10 | -2 |
| Y | +10 | 0 |
| G | 0 | 0 |
| C | 0 | 0 |
| B | 0 | 0 |

FIG.16A

MEMU        Doctor A (Name: XXX)

| Color axis | Sat. | Hue |
|---|---|---|
| M | 0 | 0 |
| R-M | −5 | +2 |
| R | +8 | +4 |
| R-Y | 0 | −2 |
| Y | +10 | 0 |
| G | 0 | 0 |
| C | 0 | 0 |
| B | 0 | 0 |

FIG.16B

MEMU        Doctor B (Name: XXX)

| Color axis | Sat. | Hue |
|---|---|---|
| M | +5 | 0 |
| R-M | +5 | 0 |
| R | +5 | 0 |
| R-Y | +5 | 0 |
| Y | +5 | 0 |
| G | 0 | 0 |
| C | 0 | 0 |
| B | 0 | 0 |

FIG.17

| Color axis | Sat. | Hue |
|---|---|---|
| M | 0 | 0 |
| R-M | −5 | +2 |
| R | +8 | +4 |
| R-Y | 0 | −2 |
| Y | +10 | 0 |
| G | 0 | 0 |
| C | 0 | 0 |
| B | 0 | 0 |

| RGB MAGNITUDE RELATIONSHIP | HUE REGION |
|---|---|
| $(2 \times B - G) > R$<br>$R \geq B \geq G$ | REGION 1A |
| $(2 \times B - G) \leq R$<br>$R \geq B \geq G$ | REGION 1B |
| $(2 \times G - B) \leq R$<br>$R \geq G \geq B$ | REGION 2A |
| $(2 \times G - B) > R$<br>$R \geq G \geq B$ | REGION 2B |
| $G \geq R \geq B$ | REGION 3 |
| $G \geq B \geq R$ | REGION 4 |
| $B \geq G \geq R$ | REGION 5 |
| $B \geq R \geq G$ | REGION 6 |

FIG.31

| RGB MAGNITUDE RELATIONSHIP | HUE REGION |
|---|---|
| $R \geq B \geq G$ | REGION 1 |
| $R \geq G \geq B$ | REGION 2 |
| $G \geq R \geq B$ | REGION 3 |
| $(2 \times B - R) \leq G$<br>$G \geq B \geq R$ | REGION 4A |
| $(2 \times B - R) > G$<br>$G \geq B \geq R$ | REGION 4B |
| $(2 \times G - R) > B$<br>$B \geq G \geq R$ | REGION 5A |
| $(2 \times G - R) \leq B$<br>$B \geq G \geq R$ | REGION 5B |
| $B \geq R \geq G$ | REGION 6 |

FIG.33A

MEMU  Normal Mode

| Color axis | Sat. | Hue |
|---|---|---|
| M | 0 | 0 |
| R-M | -5 | +2 |
| R | +8 | +4 |
| R-Y | 0 | -2 |
| Y | +10 | 0 |
| G | 0 | 0 |
| C | 0 | 0 |
| B | 0 | 0 |

FIG.33B

MEMU  AFI Mode

| Color axis | Sat. | Hue |
|---|---|---|
| M | +3 | +2 |
| R | 0 | 0 |
| Y | 0 | 0 |
| G | +5 | -4 |
| C - G | +4 | -2 |
| C | 0 | +1 |
| C - B | +8 | -2 |
| B | 0 | 0 |

FIG.33C

MEMU  NBI Mode

| Color axis | Sat. | Hue |
|---|---|---|
| M | 0 | 0 |
| R | +2 | -2 |
| Y | 0 | 0 |
| G | 0 | 0 |
| C - G | -4 | +2 |
| C | -2 | +4 |
| C - B | 0 | +7 |
| B | 0 | 0 |

FIG.34A

MEMU        SCOPE – A

| Color axis | Sat. | Hue |
|---|---|---|
| M | 0 | 0 |
| R–M | −5 | +2 |
| R | +8 | +4 |
| R–Y | 0 | −2 |
| Y | +10 | 0 |
| G | 0 | 0 |
| C | 0 | 0 |
| B | 0 | 0 |

FIG.34B

MEMU        SCOPE – B

| Color axis | Sat. | Hue |
|---|---|---|
| M | 0 | 0 |
| R–M | +2 | 0 |
| R | +4 | 0 |
| R–Y | 0 | −2 |
| Y | +6 | 0 |
| G | 0 | 0 |
| C | 0 | 0 |
| B | 0 | 0 |

FIG.35

| Color axis | Sat. | Hue |
|---|---|---|
| M | 0 | 0 |
| R-M | −5 | +2 |
| R | +8 | +4 |
| R-Y | 0 | −2 |
| Y | +10 | 0 |
| G | 0 | 0 |
| C | 0 | 0 |
| B | 0 | 0 |

ENDOSCOPE SYSTEM AND ENDOSCOPIC IMAGE PROCESSING APPARATUS

CROSS REFERENCE TO RELATED APPLICATION

This application is a continuation application of PCT/JP2009/067806 filed on Oct. 14, 2009 and claims benefit of Japanese Applications No. 2008-268852 filed in Japan on Oct. 17, 2008, No. 2008-268853 filed in Japan on Oct. 17, 2008, the entire contents of each of which are incorporated herein by their reference.

BACKGROUND OF THE INVENTION

1. Field of the Invention

The present invention relates to an endoscope system and an endoscopic image processing apparatus which output endoscopic images subjected to a color correction process and, more particularly, to an endoscope system and an endoscopic image processing apparatus which perform the color correction process using more than six color axes in a color space.

2. Description of the Related Art

Endoscope systems are widely used to observe a target in an object under examination which does not lend itself to direct visual inspection by a surgeon. In the field of medicine, diagnosis is carried out based on endoscopic images shot under irradiating light from a light source device by an image pickup unit of an endoscope inserted into a body of a subject that is an object under examination. Color reproduction of endoscopic images, i.e., the extent to which original colors are reproduced faithfully, is important because of a great impact the color reproduction can have on diagnostic results. Therefore, a color correction process is performed on a video signal in an image processing unit of a processor connected with the endoscope.

As a color tone correction scheme which provides good color reproduction, an independent 6-color color-tone correction scheme is known. The independent 6-color color-tone correction scheme adjusts chroma and hue, i.e., performs a color correction process, which is color tone adjustment, with respect to each of hue regions partitioned by reference color axes (hereinafter also referred to as "reference axes" or "color axes") of six colors—R (red), M (magenta), B (blue), C (cyan), G (green), and Y (yellow)—without changing white balance, i.e., without adding color to an achromatic-color signal. The phrase "with respect to each of hue regions," as referred to herein, means that only two hue regions on both sides of a given color axis is affected.

However, with the independent 6-color color-tone correction scheme, although colors close to any of six colors R, M, B, C, G, and Y can be adjusted effectively, intermediate colors therebetween cannot be adjusted sufficiently.

On the other hand, in order to make fine corrections of intermediate colors as well, a color correction apparatus proposed in Japanese Patent Application Laid-Open Publication No. 9-247701 further divides colors and performs a color correction process with respect to each of color spaces resulting from division by seven color axes made up of six reference color axes corresponding to the six colors in a color space and an auxiliary color axis between an R axis and a Y axis.

Also, a color correction apparatus proposed in Japanese Patent Application Laid-Open Publication No. 2001-61160 further divides colors and performs a color correction process using 12 color axes made up of six reference color axes corresponding to the six colors in the color space and six additional reference color axes established between each pair of reference color axes.

Medical endoscope systems use various types of endoscope and light source device according to purposes. Also, endoscopic images vary greatly in color tone depending on the type of observed site. Moreover, even the same site shows substantial change in color tone if, for example, bleeding occurs. Besides, when carrying out diagnosis based on comparison with endoscopic images shot in the past, it is preferable to use endoscopic images of the same color tone as the past endoscopic images. Furthermore, each surgeon has a taste in color tones, and processing conditions for a color correction process need to be adjusted to suite the taste of the surgeon before use.

Endoscope systems which have been put to practical use include an endoscope system which operates in a normal-light imaging mode, obtains endoscopic images by shooting tissue in a living body using normal light such as white color as irradiating light, and displays the obtained endoscopic images on a monitor or the like for observation.

An endoscope system which operates in a special-light imaging mode to obtain endoscopic images by taking shots using special light as irradiating light makes it easier to distinguish between normal tissue and diseased tissue such as a tumor. For example, an endoscope system of narrow band imaging mode is used, where the narrow band imaging mode uses irradiating light whose spectral transmittance characteristics have a narrowed bandwidth. Furthermore, an endoscope system of auto fluorescence imaging mode is known, where the auto fluorescence imaging mode photographs fluorescence produced when an observed site is irradiated and exited with excitation light from a light source. The endoscope system of the auto fluorescence imaging mode uses a technique for shooting an oncotropic fluorescent substance administered to an observed site or a technique for shooting auto fluorescence which naturally occurs in a living body. Incidentally, functions of the endoscope system of the normal-light imaging mode and functions of the endoscope system of the special-light imaging mode can be implemented in a single endoscope system by changing wave length of the irradiating light supplied from the light source device.

SUMMARY OF THE INVENTION

To achieve the above object, according to an embodiment of the present invention, there is provided an endoscope system including: an endoscope equipped with an insertion portion inserted into a body of a subject, and an image pickup unit disposed at a distal end portion of the insertion portion; an illumination unit which, being detachably connected to the endoscope, illuminates the inside of the body of the subject; an imaging mode input unit used to set imaging mode of the endoscope to one of normal-light mode and special-light mode; a processing condition selection unit which selects, based on the imaging mode, a processing condition for a color correction process of an endoscopic image picked up by the image pickup unit; and a processor detachably connected to the endoscope and equipped with an image processing unit which performs the color correction process, under the processing condition selected by the processing condition selection unit, with respect to each of hue regions partitioned by at least eight reference color axes including six reference color axes which divide a color space into R (red), M (magenta), B (blue), C (cyan), G (green), and Y (yellow) hue regions and at least two reference color axes established additionally based on the imaging mode.

That is, the endoscope system according to the embodiment of the present invention includes: an endoscope equipped with an insertion portion inserted into a body of a subject, and image pickup means disposed at a distal end portion of the insertion portion; illumination means which, being detachably connected to the endoscope, illuminates the inside of the body of the subject; an imaging mode input unit used to set imaging mode of the endoscope to one of normal-light mode and special-light mode; processing condition selection means which selects, based on the imaging mode, a processing condition for a color correction process of an endoscopic image picked up by the image pickup means; and a processor detachably connected to the endoscope and equipped with image processing means which performs the color correction process, under the processing condition selected by the processing condition selection means, with respect to each of hue regions partitioned by at least eight reference color axes including six reference color axes which divide a color space into R (red), M (magenta), B (blue), C (cyan), G (green), and Y (yellow) hue regions and at least two reference color axes established additionally based on the imaging mode.

According to another embodiment of the present invention, there is provided an endoscopic image processing apparatus including: an imaging mode input unit used to set imaging mode of an endoscope to one of normal-light mode and special-light mode; a processing condition selection unit which selects a processing condition for a color correction process of an endoscopic image based on the imaging mode; and an image processing unit which performs the color correction process, under the processing condition selected by the processing condition selection unit, with respect to each of hue regions partitioned by at least eight reference color axes including six reference color axes which divide a color space into R (red), M (magenta), B (blue), C (cyan), G (green), and Y (yellow) hue regions and at least two reference color axes established additionally based on the imaging mode.

That is, the endoscopic image processing apparatus according to the other embodiment of the present invention includes: imaging mode input means used to set imaging mode of an endoscope to one of normal-light mode and special-light mode; processing condition selection means which selects a processing condition for a color correction process of an endoscopic image based on the imaging mode; and image processing means which performs the color correction process, under the processing condition selected by the processing condition selection means, with respect to each of hue regions partitioned by at least eight reference color axes including six reference color axes which divide a color space into R (red), M (magenta), B (blue), C (cyan), G (green), and Y (yellow) hue regions and at least two reference color axes established additionally based on the imaging mode.

BRIEF DESCRIPTION OF THE DRAWINGS

FIG. 8A shows an example of a processing condition for a specific type of endoscope, where the processing condition is stored in a processing condition storage unit according to the first embodiment;

FIG. 8B shows an example of a processing condition for a specific type of endoscope, where the processing condition is stored in the processing condition storage unit according to the first embodiment;

FIG. 13A shows an example of a processing condition for a specific type of illumination unit, where the processing condition is stored in the processing condition storage unit according to the first embodiment;

FIG. 13B shows an example of a processing condition for a specific type of illumination unit, where the processing condition is stored in the processing condition storage unit according to the first embodiment;

FIG. 14A shows an example of a processing condition for a specific site, where the processing condition is stored in the processing condition storage unit according to the first embodiment;

FIG. 14B shows an example of a processing condition for a specific site, where the processing condition is stored in the processing condition storage unit according to the first embodiment;

FIG. 15A shows an example of a processing condition for a specific scene, where the processing condition is stored in the processing condition storage unit according to the first embodiment;

FIG. 15B shows an example of a processing condition for a specific scene, where the processing condition is stored in the processing condition storage unit according to the first embodiment;

FIG. 16A shows an example of a processing condition for a specific surgeon, where the processing condition is stored in the processing condition storage unit according to the first embodiment;

FIG. 16B shows an example of a processing condition for a specific surgeon, where the processing condition is stored in the processing condition storage unit according to the first embodiment;

FIG. 17 shows an example of a display screen used to correct processing conditions according to the first embodiment;

FIG. 31 is an explanatory diagram for illustrating 8-axis color correction performed on the endoscope system according to the fourth embodiment;

FIG. 33A shows an example of a processing condition for a specific type of illuminating light, where the processing condition is stored in a processing condition storage unit;

FIG. 33B shows an example of a processing condition for a specific type of illuminating light, where the processing condition is stored in the processing condition storage unit;

FIG. 33C shows an example of a processing condition for a specific type of illuminating light, where the processing condition is stored in the processing condition storage unit;

FIG. 34A shows an example of a processing condition for a specific type of endoscope, where the processing condition is stored in the processing condition storage unit;

FIG. 34B shows an example of a processing condition for a specific type of endoscope, where the processing condition is stored in the processing condition storage unit; and FIG. 35 shows an example of a display screen used to correct processing conditions for the endoscope system according to the fourth embodiment.

DETAILED DESCRIPTION OF THE PREFERRED EMBODIMENTS

<First Embodiment>

An endoscope system 1 according to a first embodiment of the present invention will be described below with reference to the drawings.

Figure 1:
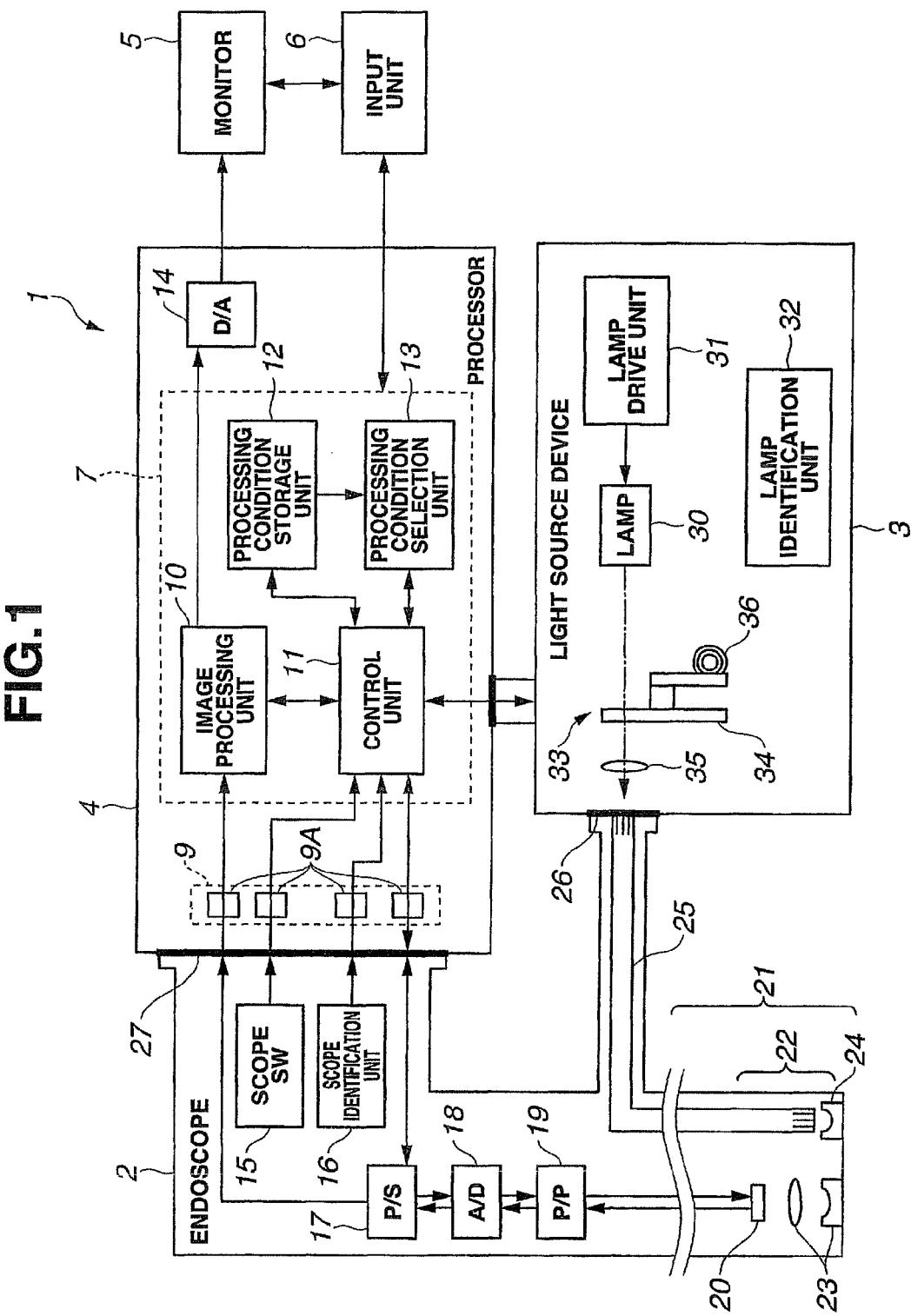
FIG. 1 is a block diagram showing a configuration of an endoscope system according to a first embodiment.

FIG. 1 is a block diagram showing a configuration of the endoscope system 1 according to the present embodiment. As shown in FIG. 1, the endoscope system 1 according to the present embodiment includes an endoscope (also referred to as a "scope") 2 equipped with an insertion portion 21 inserted into the body of a subject (not shown) which is an object under examination, a light source device 3 which is illumination means which illuminates the inside of the body of the subject, and a processor 4 which performs signal processing on endoscopic images. The endoscope 2 is detachably connected with the light source device 3 via a light source device connector unit 26, and detachably connected with the processor 4 via a processor connector unit 27. That is, the processor 4 can be used as an endoscope system which suits various purposes if used in combination with various endoscopes and/or various light source devices.

Furthermore, the endoscope system 1 includes a monitor 5 which displays endoscopic images and the like and an input unit 6, such as a keyboard, which is input means used by a surgeon to make settings and the like of the endoscope system 1.

The endoscope 2 is an electronic endoscope which includes a CCD 20, a preprocessing unit 19, an A/D conversion unit 18, and a parallel/serial (P/S) conversion unit 17, where the CCD 20 is image pickup means which shoots color endoscopic images by being installed at a distal end portion 22 of the insertion portion 21. An observation window (not shown) is provided in the distal end portion 22. An objective lens system 23 adapted to form an optical image and the CCD 20 adapted to take shots in the body of the subject are placed in the observation window. The endoscopic images shot by the CCD 20 are converted into a digital signal and transmitted to the processor 4. The image pickup means may be a CMD (Charge Modulation Device) image pickup device, a C-MOS image pickup device, an AMI (Amplified MOS Imager), a BCCD (Back Illuminated CCD), or the like instead of the CCD 20. Incidentally, irradiating light may be changed to RBG in time sequence using a monochrome CCD instead of a color CCD.

Furthermore, a light guide fiber 25 is passed through the insertion portion 21 to guide illuminating light from the light source device 3 to the distal end portion 22. The light source device 3 includes a lamp 30 which emits light by being driven by a lamp drive unit 31, a filter wheel unit 33 provided on a light path of the lamp 30, and a condenser lens 35 which condenses the light passing through the filter wheel unit 33. The filter wheel unit 33 includes a filter wheel 34 which switches among its filters to place an appropriate filter on the light path when rotated by a rotation motor 36. The illuminating light guided to the distal end portion 22 by the light guide fiber 25 is spread after passing through an illumination lens 24 mounted in an illuminating window (not shown) and is directed at a site to be observed in the body. Furthermore, a lamp identification unit 32 is disposed in the light source device 3, where the lamp identification unit 32 is light source identification means for identifying the type of the light source device 3 connected with the processor 4, in other words, the type of the light source device 3 connected with the endoscope 2.

Also, the endoscope 2 is provided with a scope switch 15 for use by the surgeon to give various operating commands to the endoscope system 1 via fingertip control. An operation signal from the scope switch 15 is inputted into a control unit 11, which then performs an action according to the operation signal. Furthermore, the endoscope 2 is provided with a scope identification unit 16 which is scope identification means for identifying the type of the endoscope 2 connected with the processor 4.

An endoscopic image signal from the endoscope 2 is inputted into an endoscopic image processing apparatus 7 of the processor 4 via an isolation unit 9 made up of a pulse transformer 9A or the like provided to ensure insulation. The endoscopic image processing apparatus 7 includes an image processing unit 10, the control unit 11, a processing condition storage unit 12, a processing condition selection unit 13, and a D/A conversion unit (D/A) 14, where the image processing unit 10 is image processing means which performs a color correction process and the like on endoscopic images shot by the CCD 20, the control unit 11 controls the endoscope system 1 including the endoscopic image processing apparatus 7, the processing condition storage unit 12 is processing condition storage means which stores processing conditions for the color correction process performed by the image processing unit 10, and the processing condition selection unit 13 is processing condition selection means which selects a processing condition in the processing condition storage unit 12. The color correction process of endoscopic images will be described later.

Figure 2:
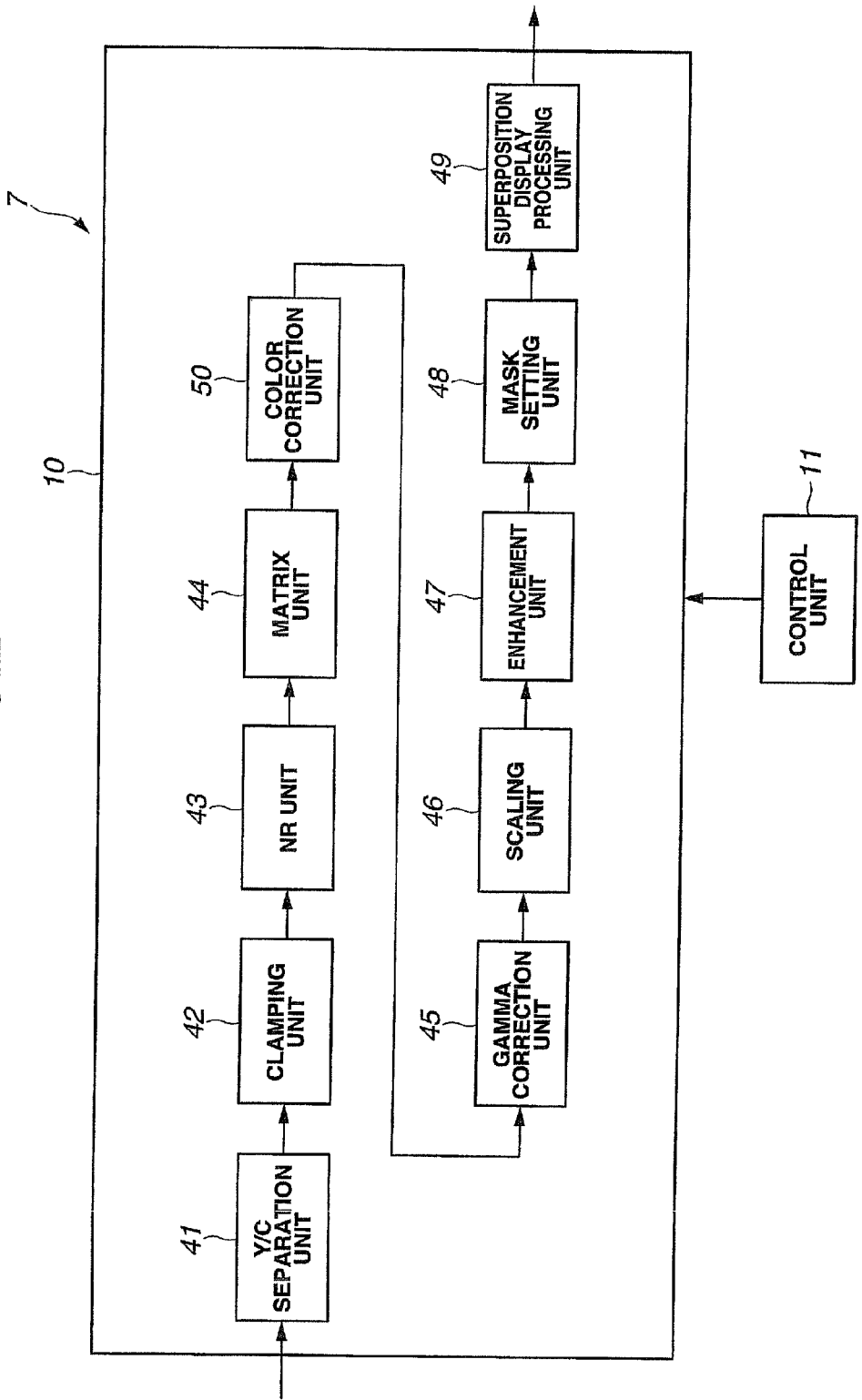
FIG. 2 is a block diagram for illustrating image processing performed by an endoscopic image processing apparatus according to the first embodiment.

Next, image processing of endoscopic images performed by the image processing unit 10 of an endoscopic image processing apparatus 7 will be described with reference to FIG. 2. FIG. 2 is a block diagram for illustrating image processing performed by the endoscopic image processing apparatus 7 according to the present embodiment.

As shown in FIG. 2, an endoscopic image signal from the endoscope 2 is subjected to a color correction process by a color correction processing unit 50 via a Y/C separation unit 41, a clamping unit 42, a noise reduction (NR) unit 43, and a matrix unit 44. The endoscopic image subjected to the color correction process is transmitted to the D/A conversion unit 14 via a gamma correction unit 45, a scaling unit 46, an enhancement unit 47, a mask setting unit 48, and a superposition display processing unit 49 and displayed on the monitor 5. All processes of the image processing unit 10 are performed under the control of the control unit 11.

Figures 3, 4:
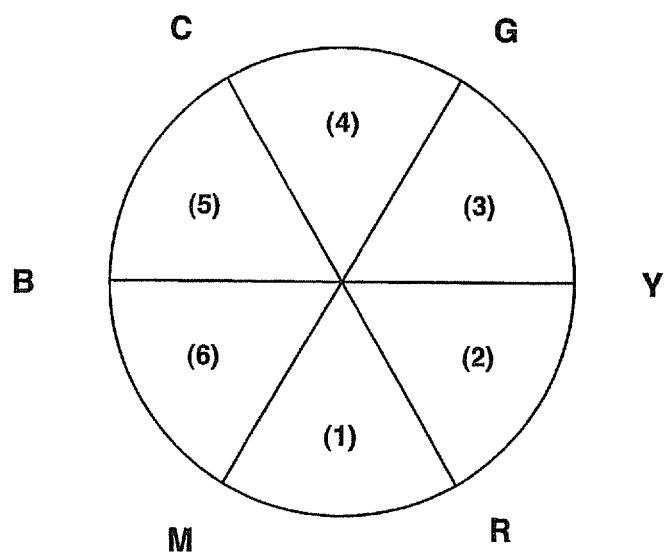
FIG. 3 is an explanatory diagram for illustrating 6-axis color correction.
FIG. 4 is an explanatory diagram for illustrating 6-axis color correction.
Figures 5, 6:
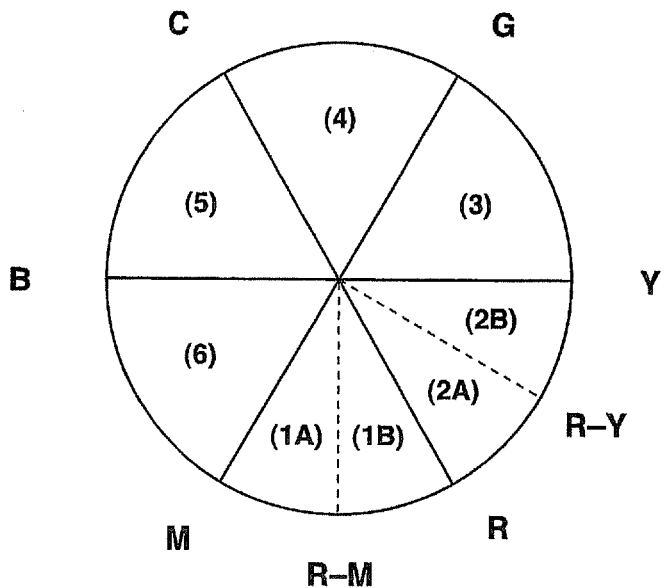
FIG. 5 is an explanatory diagram for illustrating 8-axis color correction performed on the endoscopic image processing apparatus according to the first embodiment.
FIG. 6 is an explanatory diagram for illustrating 8-axis color correction performed on the endoscopic image processing apparatus according to the first embodiment.
Figure 7:
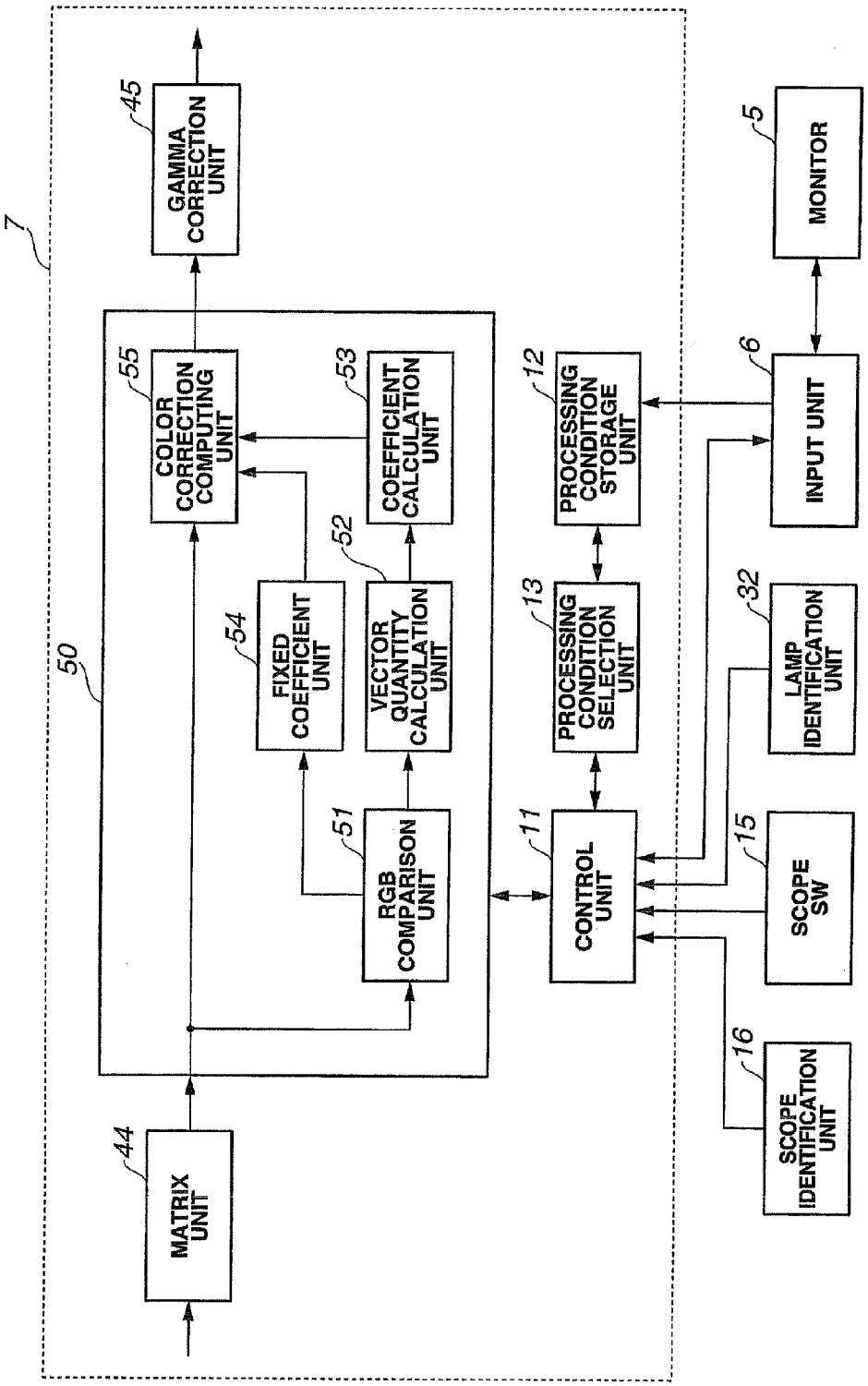
FIG. 7 is a block diagram for illustrating a color correction process performed by a color correction processing unit of the endoscopic image processing apparatus according to the first embodiment.
Figure 9:
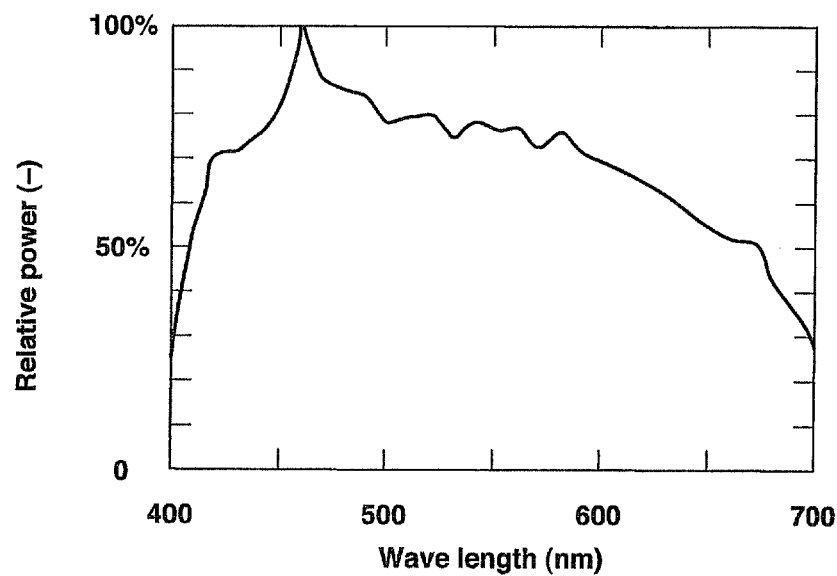
FIG. 9 shows spectrophotometric characteristics of a xenon lamp.
Figure 10:
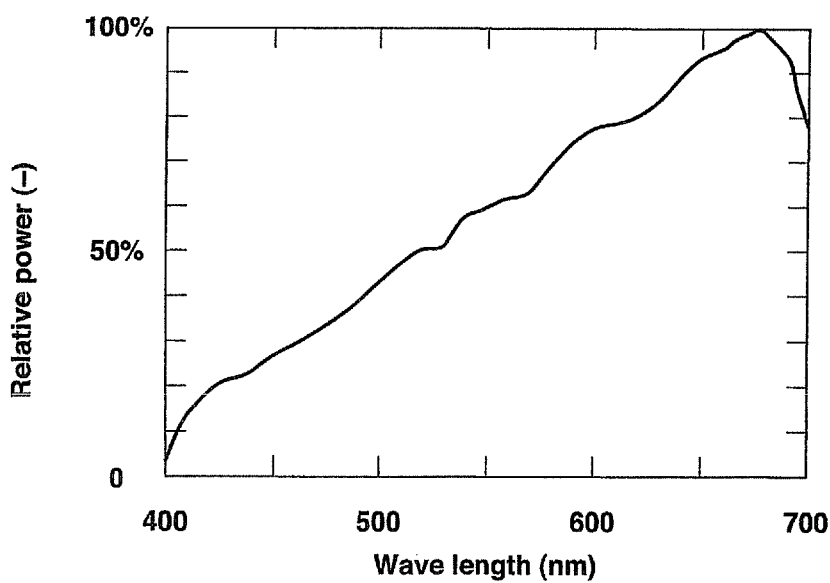
FIG. 10 shows spectrophotometric characteristics of a halogen lamp.
Figure 11:
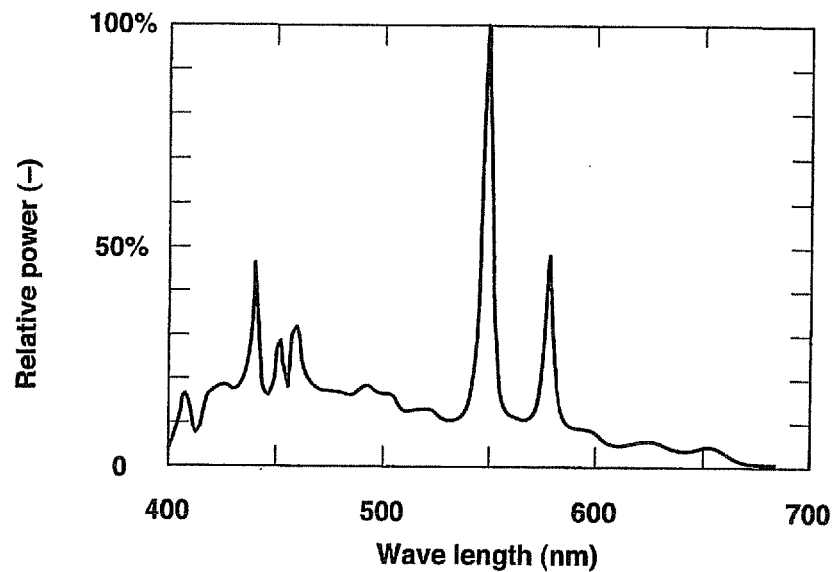
FIG. 11 shows spectrophotometric characteristics of a metal halide lamp.
Figure 12:
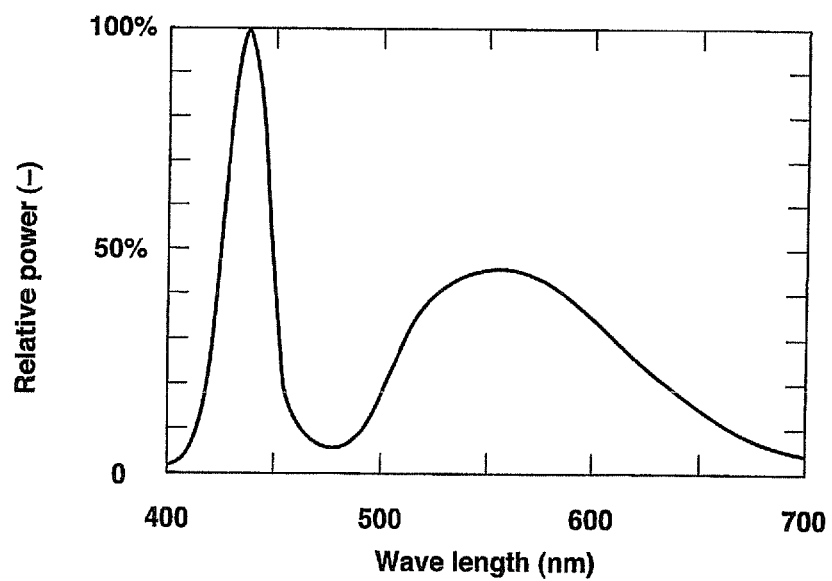
FIG. 12 shows spectrophotometric characteristics of a light-emitting diode.

Next, the color correction process performed by the color correction processing unit 50 will be described with reference to FIGS. 3 to 9. FIGS. 3 and 4 are explanatory diagrams for illustrating 6-axis color correction. FIGS. 5 and 6 are explanatory diagrams for illustrating 8-axis color correction performed on the endoscopic image processing apparatus 7 according to the present embodiment. FIG. 7 is a block diagram for illustrating the color correction process performed by the color correction processing unit 50 of the endoscopic image processing apparatus 7 according to the present embodiment.

FIG. 3 shows six hue regions (1) to (6) partitioned by six reference color axes established respectively for hues R (red), M (magenta), B (blue), C (cyan), G (green), and Y (yellow) in a color space. That is, the color axes established radially from the center point of the color space shown in FIG. 3 represent intensity of chroma (hereinafter also referred to as "color saturation" or simply as "saturation" and denoted by symbol "sat"). The color saturation increases outwardly from the center of a color circle. Also, a circumferential direction of the color space represents hue (hereinafter denoted by symbol "hue").

As shown in FIG. 4, a so-called 6-axis color correction process involves determining in which of the six hue regions an image signal to be subjected to the color correction process is located, based on magnitude relationship among an R signal, a G signal, and a B signal, and the hue region in which the image signal is located is corrected. That is, colors of the color axes on both sides of the hue region in which the image signal is located are corrected. Therefore, when a pixel belonging to a hue region is corrected, three hue regions centering around the hue region to which the pixel belongs are affected, but the hue regions on both sides of the hue region to which the pixel belongs are not affected much.

On the other hand, FIG. 5 shows a color space for a so-called 8-axis color correction process according to the present embodiment, in which two reference color axes are established in the color space in addition to the six reference color axes. Since the endoscope system 1 according to the present embodiment is used to make observations in the body of the subject, the endoscopic images shot by the CCD 20 often have a subtle color tone centering around red color. Therefore, as shown in FIG. 5, in the endoscope system 1, an R-Y color axis and an R-M color axis—one reference color axis each—are established between an R reference color axis and a Y reference color axis and between an R reference color axis and an M reference color axis. Consequently, in the 8-axis color correction process, eight hue regions (1A), (1B), (2A), (2B), (3), (4), (5), and (6) are divided by the color axes.

If, for example, a correction coefficient is changed during the correction process of the R-M color axis, the region (1A) and the region (1B) on both sides of the R-M color axis are affected. Therefore, for example, when pixels belonging to the region (1B) are color corrected with respect to each hue region, three hue regions—not only the region (1B), but also the region (1A) and the region (2A)—are affected, but the region (1A) and the region (2A) are affected less, and the remaining regions are not affected.

As shown in FIG. 6, it is determined in which of the eight hue regions a pixel color signal of an endoscopic image is located, based on magnitude relationship among an R signal, a G signal, and a B signal, and the hue region thus determined is color corrected. Being designed as an endoscopic image processing apparatus which performs a color correction process based on eight axes including reference color axes which represent RGB primary colors and reference color axes which represent complementary colors CMY of the primary colors as well as a reference color axis which represents an intermediate color between R and Y and a reference color axis which represents an intermediate color between R and M needed to finely correct colors around R contained in large quantities in the body which is a conceivable object to be photographed, the endoscope system 1 lends itself to easy equipment design and minimizes complexity of circuits and the like.

Next, the color correction process performed by the color correction processing unit 50 of the endoscopic image processing apparatus 7 according to the present embodiment will be described with reference to FIG. 7. The endoscopic image inputted into the color correction processing unit 50 from the matrix unit 44 is made up of a color signal which in turn is made up of an R signal, a G signal, and a B signal. As shown in FIG. 6, an RGB comparison unit 51 determines in which of the eight hue regions the color signal of each pixel making up the endoscopic image is located, based on magnitude relationship among the R signal, the G signal, and the B signal.

In order to perform a color correction process with respect to each of the eight hue regions, the processing condition storage unit 12 prestores processing conditions each of which is made up of eight saturation (chroma) correction coefficients KRsat, KGsat, KBsat, KYsat, KCsat, KMsat, KRYsat, and KRMsat as well as eight hue correction coefficients KRhue, KGhue, KBhue, KYhue, KChue, KMhue, KRYhue, and KRMhue. The subscript following the symbol "K" which represents the correction coefficients is an abbreviation of hue. Also, RM represents an intermediate color between R and M while RY represents an intermediate color between R and Y.

Based on set values of the processing condition received from the processing condition selection unit 13 and results produced by the RGB comparison unit 51, the control unit 11 outputs four correction coefficients Ksat1, Ksat2, Khue1, and Khue2 to the color correction processing unit 50, where the four correction coefficients make up a processing condition for the hue region in which the color signal of the pixel of the endoscopic image is located. On the other hand, a vector quantity calculation unit 52 of the color correction processing unit 50 calculates vector quantities Dp and Dc of the color signal of the pixel of the endoscopic image in a color axis direction on both sides of the hue region in which the color signal of the pixel is located. Based on the processing condition received from the control unit 11 and the vector quantities calculated by the vector quantity calculation unit 52, a coefficient calculation unit 53 calculates the correction coefficients using Expression 1 below.

$$R_{out}=R_{in}+p_{sat}+(p_{hue}-R_{-a1})+c_{sat}+(c_{hue}+R_{-a2})$$

$$G_{out}=G_{in}+p_{sat}+(p_{hue}\times G_{-a1})+c_{sat}+(C_{hue}+G_{-a2})$$

$$B_{out}=B_{in}+p_{sat}+(p_{hue}\times B_{-a1})+c_{sat}+(c_{hue}+B_{-a2}) \quad \text{(Expression 1)}$$

Based on fixed correction coefficients R–a1, G–a1, B–a1, R–a2, G–a2, and B–a2 received from a fixed coefficient unit 54 as well as the calculated correction coefficients psat, phue, csat, and chue received from the coefficient calculation unit 53, a color correction computing unit 55 performs a color correction process on the endoscopic image using Expression 2 below, and outputs results to the gamma correction unit 45 in a subsequent stage.

$$p_{sat}=K_{sat1}\times d_p$$

$$p_{hue}=K_{hue1}\times d_p$$

$$c_{sat}=K_{sat2}\times d_c$$

$$c_{hue}=K_{hue2}\times d_c \quad \text{(Expression 2)}$$

In the color correction process of the endoscope system 1, the processing condition selection unit 13 selects an optimal processing condition for the endoscopic image from the processing conditions made up of the eight saturation correction coefficients and the eight hue correction coefficients stored in the processing condition storage unit 12. Specifically, the processing condition selection unit 13 selects the processing condition based on the information received from the scope identification unit 16, the scope switch 15, the lamp identification unit 32, the input unit 6, the monitor 5, or the like via the control unit. This makes it easy for the endoscope system 1 to appropriately set correction conditions used by the image processing unit 10.

For example, in the endoscope system 1, the processing condition selection unit 13 selects the processing condition according to the type of endoscope 2. The type of endoscope 2 does not mean a model or the like. Since there are differences in color characteristics even among products of the same model due to variations in manufacturing processes, each individual endoscope 2 constitutes a type. Especially with regard to color CCDs, there are large differences in characteristics even among products of the same model due to variations in manufacture of color filters. Therefore, preferably the processing condition selection unit 13 selects a processing condition for each endoscope. The processing condition selection unit 13 identifies the type of endoscope, in other words, the individual endoscope connected to the processor 4, based on information from the scope identification unit disposed in the endoscope 2.

Examples of processing conditions for specific types of endoscope are shown in FIGS. 8A and 8B, where the processing conditions are stored in the processing condition storage unit 12. FIG. 8A shows a processing condition for endoscope A and FIG. 8B shows a processing condition for endoscope B. The correction coefficients are expressed in relative values represented, for example, by integers between –100 and 100.

In the endoscope system 1, the processing condition selection unit 13 selects a processing condition based on the type of light source device 3 which is light source means. The type of light source device 3, as referred to herein, is the type of lamp 30 and can be, for example, xenon lamp, halogen lamp, metal halide lamp, or light-emitting diode.

Spectrophotometric characteristics vary with the type of lamp 30 as shown in FIGS. 9 to 12, and thus reflected light in the subject varies with the type of light source device 3, and so does the color tone of the endoscopic image. Examples of processing conditions for specific types of light source device 3 are shown in FIGS. 13A and 13B, where the processing conditions are stored in the processing condition storage unit 12. FIG. 13A shows a processing condition for a xenon lamp and FIG. 13B shows a processing condition for a light-emitting diode (LED).

In the endoscope system 1, since the processing condition selection unit 13 selects processing conditions based on the type of light source device 3, it is easy to appropriately set the correction conditions used by the image processing unit 10.

Of course, the type of light source device 3 does not mean only the type of lamp 30. Since there are differences in characteristics even among products of the same model due to variations in manufacturing processes, each individual light source device 3 may have an identification sign which corresponds to a type.

Also, the endoscope system 1 includes a body site input unit which is body site input means for selecting a body site to be photographed by the CCD 20, and the processing condition selection unit 13 selects the processing condition based on the body site selected by the body site input unit. The site is any of the otolaryngological organs, the esophagus, the stomach, the small intestine, the large intestine, and the abdominal cavity. The color tone of the endoscopic image varies with the site. Examples of processing conditions for specific sites are shown in FIGS. 14A and 14B, where the processing conditions are stored in the processing condition storage unit 12. FIG. 14A shows a processing condition for the stomach and FIG. 14B shows a processing condition for the otolaryngological organs.

In the endoscope system 1, since the processing condition selection unit 13 selects processing conditions based on the site to be photographed, it is easy to appropriately set the correction conditions used by the image processing unit 10.

As the body site input unit, the input unit 6 used by the surgeon to enter inputs or the scope switch 15 can be used, for example. Alternatively, for example, a method based on image analysis of endoscopic images or a method based on a position sensor or the like may be used for the body site input unit.

Also, the endoscope system 1 includes a scene input unit which is scene input means used to select a scene according to conditions in the body, and the processing condition selection unit 13 selects the processing condition based on the scene selected via the body site input unit. The scene is either a normal scene or a bleeding scene. The color tone of the endoscopic image varies with the scene. As the scene input unit, the input unit 6 used by the surgeon to enter inputs or the scope switch 15 can be used, for example.

Examples of processing conditions for specific scenes are shown in FIGS. 15A and 15B, where the processing conditions are stored in the processing condition storage unit 12. FIG. 15A shows a processing condition for a normal scene and FIG. 15B shows a processing condition for a bleeding scene. The bleeding scene is an endoscopic image predominantly R (red) in color due to blood, and thus an appropriate color correction process is a so-called redless color correction process which decreases red hues. Incidentally, types of scene may be added or changed, such as adding a dye spraying scene, according to technique.

Also, the endoscope system 1 includes a surgeon specifying unit which is surgeon specifying means used to specify a surgeon. Then, based on the surgeon specified via the surgeon specifying unit, i.e., the surgeon's name, initials, identification number, or the like, the processing condition selection unit 13 selects a processing condition which suits the surgeon's taste. Examples of processing conditions for specific surgeons are shown in FIGS. 16A and 16B, where the processing conditions are stored in the processing condition storage unit 12. FIG. 16A shows a processing condition preferred by doctor A and FIG. 16B shows a processing condition preferred by doctor B. The processing condition for a specific surgeon is also the processing condition for the endoscopic images shot by the surgeon in the past.

In the endoscope system 1, since the processing condition selection unit 13 selects a processing condition needed to obtain an endoscopic image of the color tone which suits the surgeon's taste, in other words, the same processing condition as the one used for the endoscopic images shot in the past, it is easy to appropriately set the correction conditions used by the image processing unit 10. As the surgeon specifying unit, the input unit 6 or the scope switch 15 can be used, for example. The processing condition which suits the surgeon's taste may be inputted via the input unit 6 or may be the same as the previous condition.

Furthermore, in the endoscope system 1, the processing condition selection unit 13 includes a processing condition correction unit which corrects the selected processing condition. That is, as shown in FIG. 17, a numeric value of a processing condition can be corrected via the input unit 6 by selecting a location 5D of a predetermined value using a selection marker 5C while checking values displayed, for example, in the form of a table 5B on a display screen 5A of the monitor 5. The correction of the processing condition selected by the processing condition selection unit 13 enables delicate adjustments of the color tone according to circumstances. As the processing condition selection unit 13, the input unit 6 or the scope switch 15 can be used, for example. Similarly, the processing conditions to be stored in the processing condition storage unit 12 can be set using the input unit 6 or the like.

As described above, the endoscope system 1 makes it easy to appropriately set the correction conditions used by the image processing unit 10.

Incidentally, the processing condition storage unit 12 and the processing condition selection unit 13 are described above as being separate components, independent of the control unit 11 and the image processing unit 10, but may be implemented integrally with the control unit 11 or the image processing unit 10 using the same hardware as the control unit 11 or the image processing unit 10.

Also, as described above, the endoscopic image processing apparatus 7 according to the present embodiment performs a color correction process on an endoscopic image shot by the CCD 20 of the endoscope system 1 which includes the endoscope 2 equipped with the insertion portion 21 inserted into a body of a subject and the CCD 20 which is image pickup means disposed at the distal end portion 22 of the insertion portion 21, and the light source device 3 which is illumination means for illuminating the inside of the body of the subject. The endoscopic image processing apparatus 7 includes the image processing unit 10 which is image processing means for performing the color correction process on the endoscopic image shot by the CCD 20, and the processing condition selection unit 13 which selects a processing condition from the processing condition storage unit 12 which stores processing conditions for color correction processes. The image processing unit 10 performs the color correction process, under the processing condition selected by the processing condition selection unit 13, with respect to each of hue regions partitioned by eight reference color axes established for respective hues in a color space, where the hues include R (red), M (magenta), B (blue), C (cyan), G (green), and Y (yellow) as well as an intermediate hue between R and Y and an intermediate hue between R and M. The endoscopic image processing apparatus makes it easy to appropriately set the correction conditions used by the image processing unit 10.

<Second Embodiment>

Figure 18:
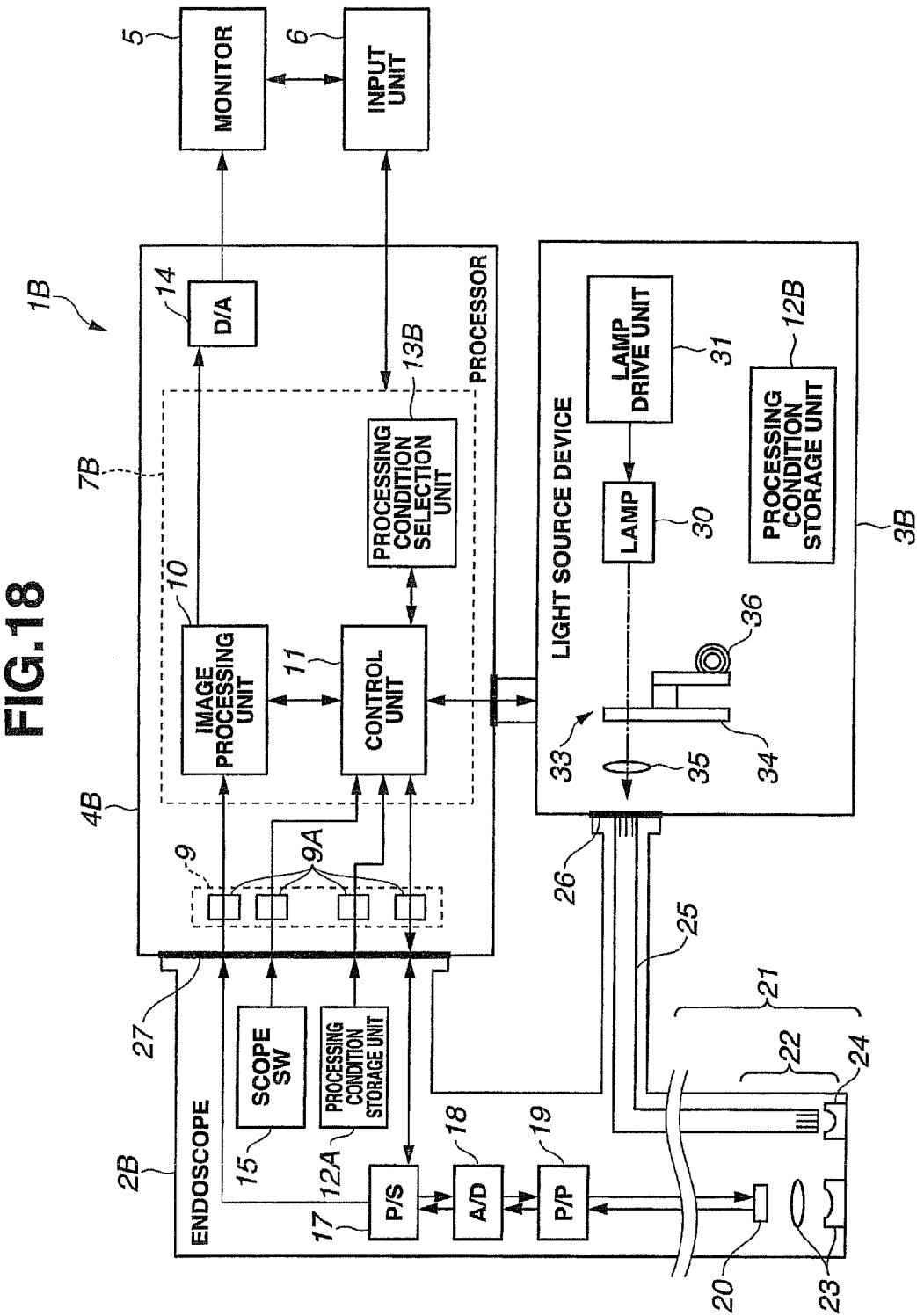
FIG. 18 is a block diagram showing a configuration of an endoscope system according to a second embodiment.

An endoscope system 1B according to a second embodiment of the present invention will be described below with reference to the drawings. FIG. 18 is a block diagram showing a configuration of the endoscope system 1B according to the second embodiment. The endoscope system 1B according to the present embodiment is similar to the endoscope system 1 according to the first embodiment. Thus, the same components as those in the first embodiment are denoted by the same reference numerals as the corresponding components in the first embodiment, and description thereof will be omitted.

With the endoscope system 1 according to the first embodiment, the endoscope 2 includes the scope identification unit 16, and the condition selection means selects a processing condition for the endoscope 2 stored in the processing condition storage unit 12 of the processor 4 based on information from the scope identification unit 16. On the other hand, as shown in FIG. 18, with the endoscope system 1B according to the present embodiment, an endoscope 2B includes a processing condition storage unit 12A which stores processing conditions suitable for the type of the endoscope 2B. Also, with the endoscope system 1B according to the present embodiment, a light source device 3B includes a processing condition storage unit 12B which stores processing conditions suitable for the light source device 3B.

With the endoscope system 1B, a processing condition selection unit 13B of an endoscopic image processing apparatus 7B selects processing conditions from at least one of the condition storage means: the processing condition storage unit 12A and the processing condition storage unit 12B.

Since the processing condition selection unit 13B selects an optimal processing condition, the endoscope system 1B makes it easy to appropriately set the correction conditions used by the image processing unit 10 in order to obtain an endoscopic image of a desired color tone.

<Third Embodiment>

Figure 19:
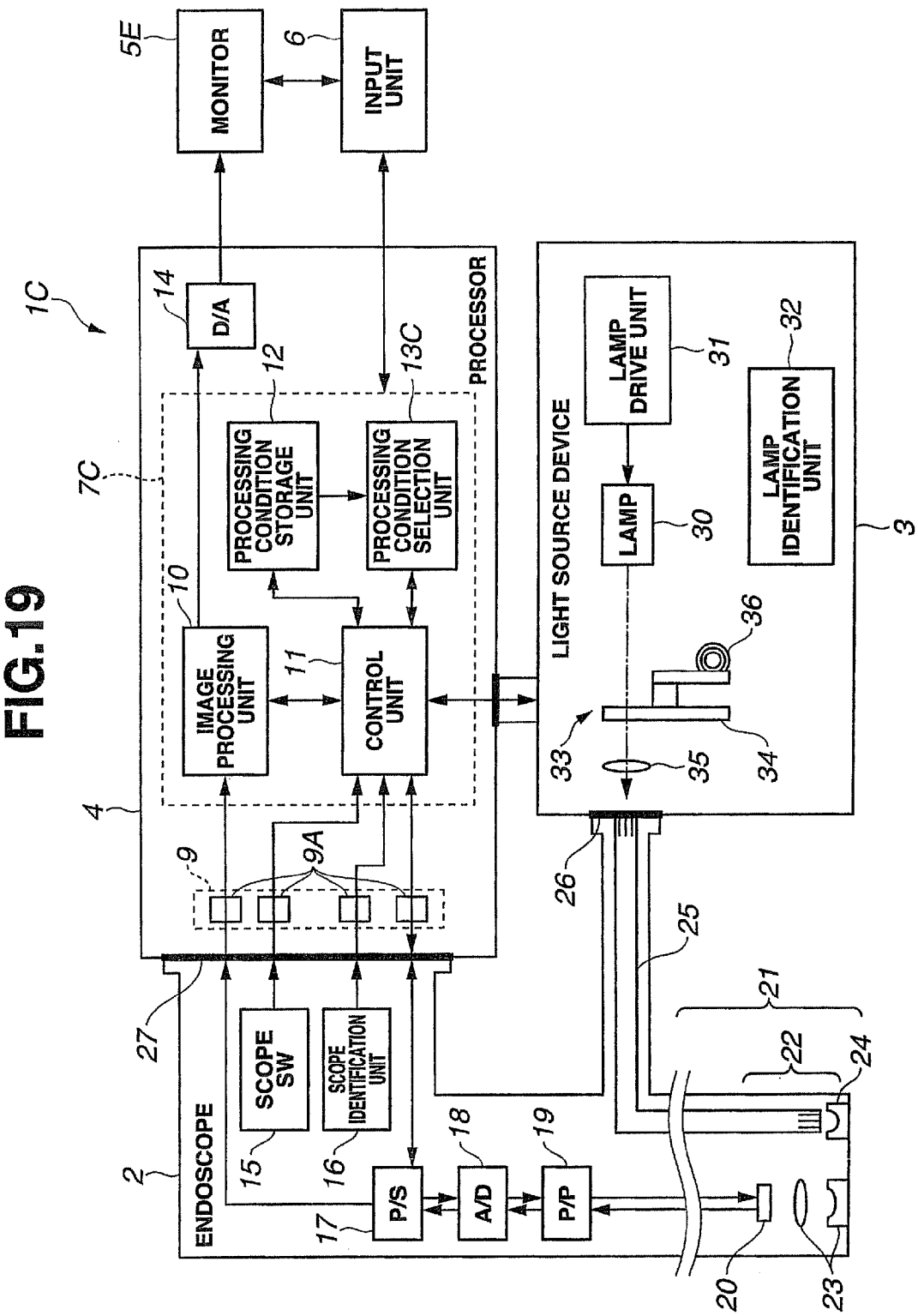
FIG. 19 is a block diagram showing a configuration of an endoscope system according to a third embodiment.

An endoscope system 1C according to a third embodiment of the present invention will be described below with reference to the drawings. FIG. 19 is a block diagram showing a configuration of the endoscope system 1C according to the third embodiment. The endoscope system 1C according to the present embodiment is similar to the endoscope system 1 according to the first embodiment. Thus, the same components as those in the first embodiment are denoted by the same reference numerals as the corresponding components in the first embodiment, and description thereof will be omitted.

With the endoscope system 1C, a processing condition selection unit 13C selects a processing condition based on multiple conditions. For example, when the type of endoscope 2 is endoscope A, the type of light source device 3 is light source device A, and the surgeon is surgeon A, the processing condition selection unit 13C of the endoscope system 1C selects processing conditions based on three conditions: endoscope A, light source device A, and surgeon A.

The processing conditions selected based on multiple conditions may be prestored in the processing condition storage unit 12. Alternatively, the processing condition selection unit 13C may perform a predetermined computational process based on the respective processing conditions for the multiple conditions and thereby calculate a processing condition suitable for the multiple conditions.

Figure 20:
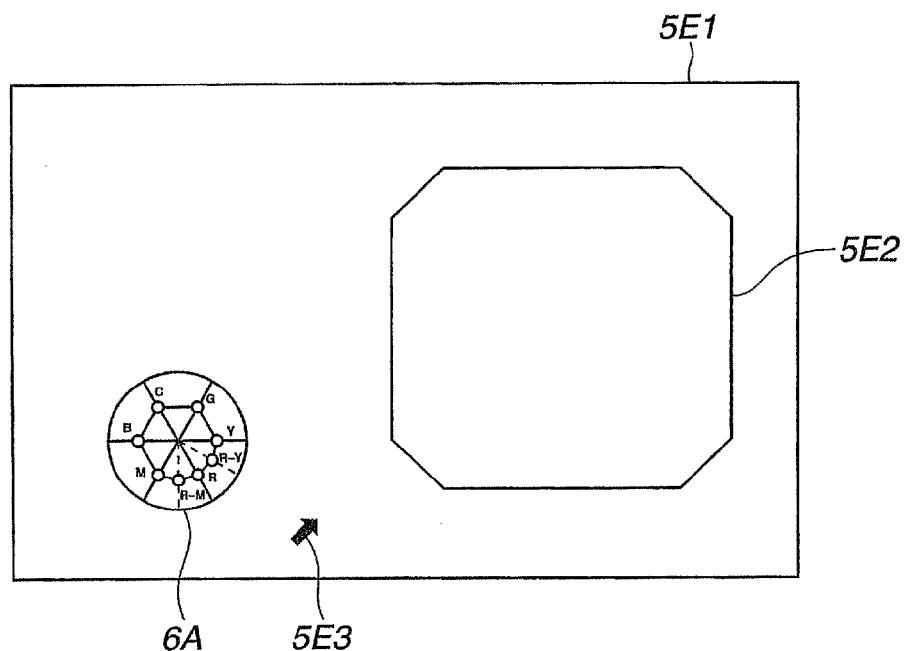
FIG. 20 is an example of a display screen of a monitor which has a graphics input unit.

Also, the endoscope system 1C can use a monitor 5E as graphics input means. FIG. 20 shows a display screen 5E1 of the monitor 5E which has functions of graphics input means. The display screen 5E1 is a 16:9 wide screen which displays an endoscopic image 5E2 subjected to a color correction process on the right, and a graphics input unit 6A for use to make settings of processing conditions on the left. The graphics input unit 6A can be operated with a pointer 5E3.

Figure 21:
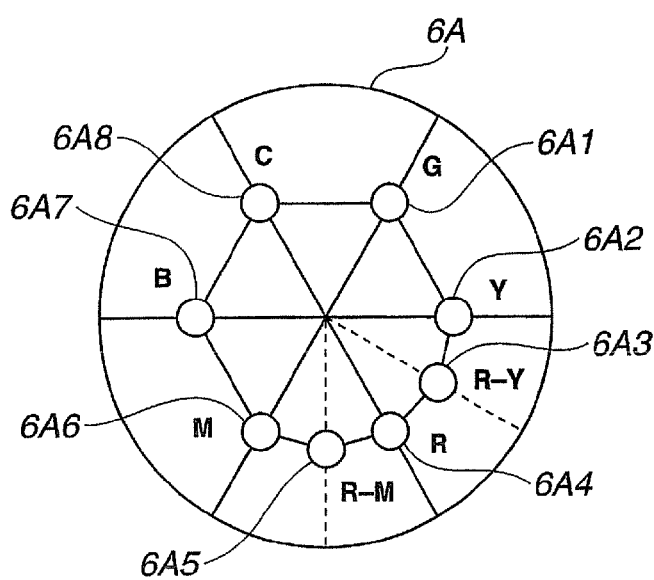
FIG. 21 is an example of the graphics input unit.

As shown in FIG. 21, the graphics input unit 6A displays a color space as a circle in color. In the color space, condition setting marks 6A1 to 6A8 are displayed, respectively, on eight reference color axes corresponding to respective hues including the hues of R (red), M (magenta), B (blue), C (cyan), G (green), and Y (yellow) as well as an intermediate hue between R and M and an intermediate hue between R and Y.

Figure 22:
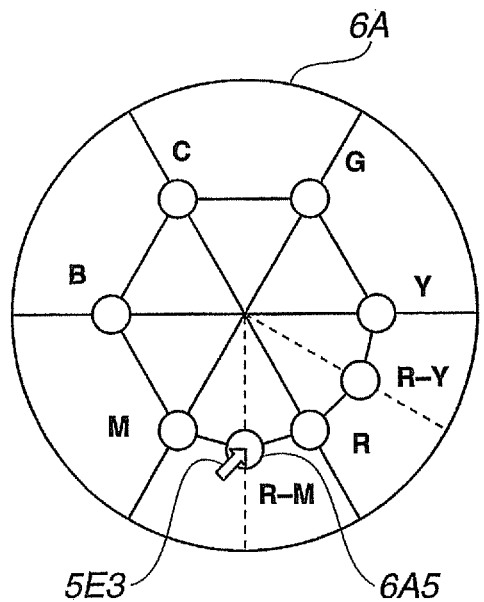
FIG. 22 is an explanatory diagram for illustrating a correction of a processing condition made via the graphics input unit.
Figure 23:
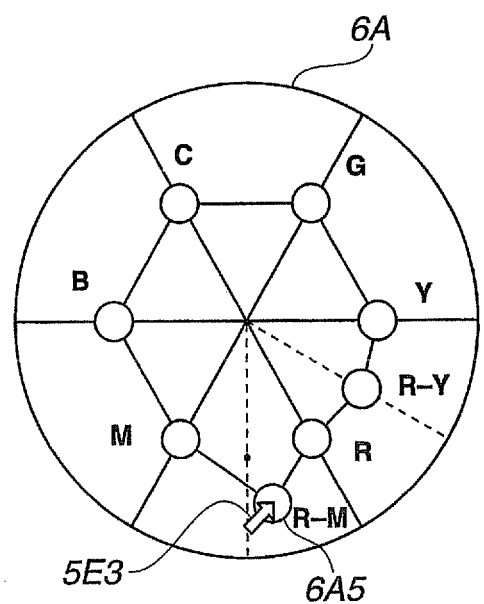
FIG. 23 is an explanatory diagram for illustrating a correction of a processing condition made via the graphics input unit.

As shown in FIGS. 22 and 23, by specifying a predetermined condition setting mark, for example, 6A5 with the pointer 5E3 using a mouse or the like and moving the condition setting mark, the surgeon can modify a setting of the processing condition. A setting range, in other words, a movable range, of each condition setting mark is, for example, between −78% and 78% of the region in a hue direction.

With the endoscope system 1C, setting changes in the processing condition via the graphics input unit 6A are reflected in the color tone of the endoscopic image in real time.

As described above, the endoscope system 1C further includes the monitor 5 which is display means for displaying the graphics input unit 6A used to make settings of a processing condition by moving the condition setting marks 6A1 to 6A8 on the reference color axes displayed in the color space as well as displaying an endoscopic image subjected to a color correction process. As settings are made for the processing condition using the condition setting marks 6A1 to 6A8, the color tone of the endoscopic image displayed on the monitor 5 changes in real time.

Thus, the endoscope system 1C allows the surgeon to easily and appropriately set the processing conditions needed to obtain an endoscopic image of a desired color tone.

<Fourth Embodiment>

An endoscope system 1D according to a fourth embodiment of the present invention will be described below with reference to the drawings. The endoscope system 1D according to the present embodiment is similar to the endoscope system 1 according to the first embodiment and the like. Thus, the same components as those in the first embodiment and the like are denoted by the same reference numerals as the corresponding components in the first embodiment and the like, and description thereof will be omitted.

Figure 24:
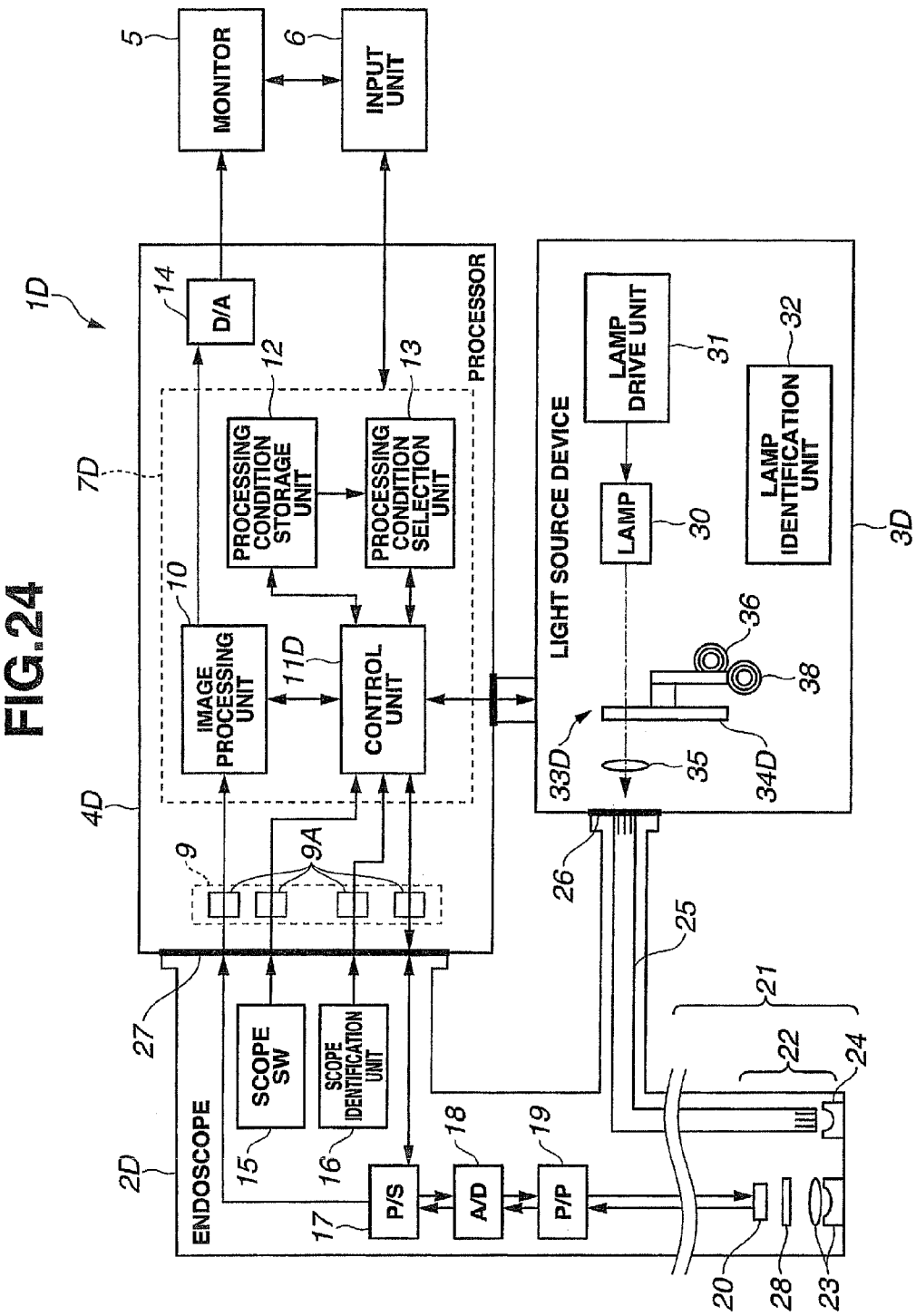
FIG. 24 is a block diagram showing a configuration of an endoscope system according to a fourth embodiment.

As shown in FIG. 24, the endoscope system 1D according to the present embodiment includes an endoscope (also referred to as a "scope") 2D equipped with an insertion portion 21 inserted into a body of a subject, a light source device 3D which is illumination means for illuminating the inside of the body of the subject with normal light or special light, and a processor 4D equipped with an endoscopic image processing apparatus 7D which performs signal processing and the like on endoscopic images. The endoscope 2D is detachably connected with the light source device 3D via a light source device connector unit 26, and detachably connected with the processor 4D via a processor connector unit 27. That is, the processor 4D can be used as an endoscope system which suits various purposes if used in combination with various endoscopes and/or various light source devices.

An objective lens system 23 adapted to form an optical image, a cut-off filter 28 adapted to pass light of a desired wave length and cut off light of the other wave lengths, and a CCD 20 adapted to take shots in the body of the subject are placed in an observation window. The endoscopic images shot by the CCD 20 are converted into a digital signal and transmitted to the processor 4D. The cut-off filter 28 is switched according to the imaging mode.

The light source device 3D includes a lamp 30 which emits light by being driven by a lamp drive unit 31, a filter wheel unit 33D provided on a light path of the lamp 30, and a condenser lens 35 which condenses light passing through the filter wheel unit 33D. The filter wheel unit 33D includes a filter wheel 34D which switches among its filters to place an appropriate filter on the light path when rotated by a rotation motor 36. The light source device 3D supplies normal light or special light as illuminating light to a light guide fiber 25 by switching the filter.

Now, the filter wheel 34D will be described with reference to FIGS. 25A, 25B, 26, and 27.

Figure 25A:
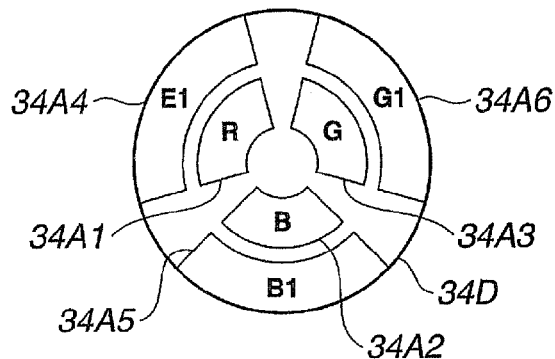
FIG. 25A is an explanatory diagram for illustrating a structure of a filter wheel for the endoscope system.
Figure 25B:
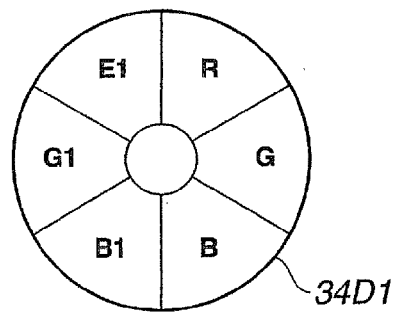
FIG. 25B is an explanatory diagram for illustrating a structure of a filter wheel for the endoscope system.

As shown in FIG. 25A, in the filter wheel 34D, an R filter 34A1, a G filter 34A2, and a B filter 34A3 for normal-light imaging mode are placed on an inner circumferential side while an E1 filter 34A4, a G1 filter 34A5, and a B1 filter 34A6 for special-light imaging mode are placed on an outer circumferential side. Incidentally, a filter wheel 34D1 with a filter layout such as shown in FIG. 25B may be used instead of the filter wheel 34D. Alternatively, multiple filter wheels may be used.

Figure 26:
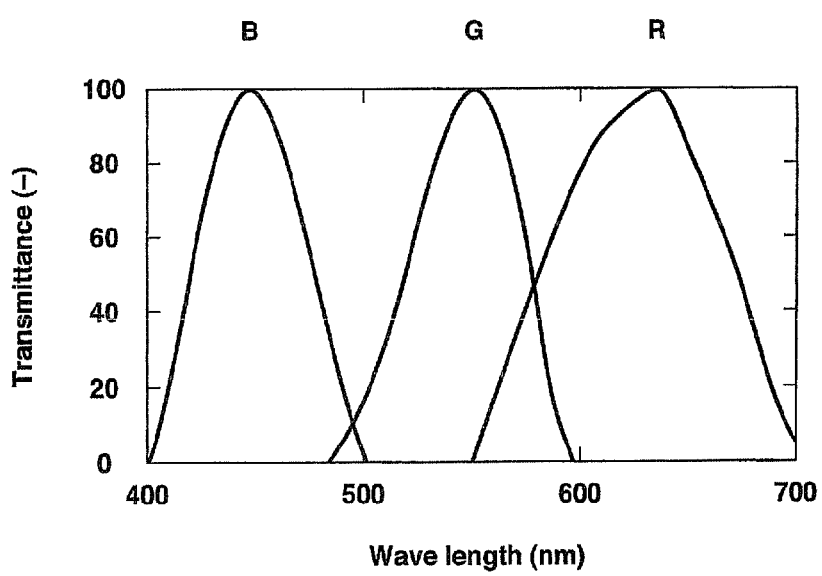
FIG. 26 is a graph showing transmittance characteristic vs. filter wave length.
Figure 27:
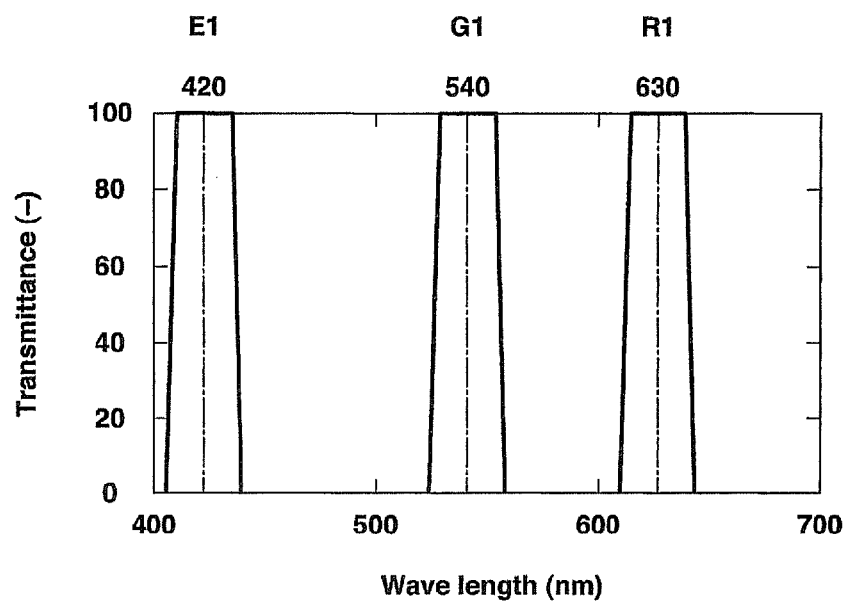
FIG. 27 is a graph showing transmittance characteristic vs. filter wave length according to an embodiment.

FIG. 26 shows an example of transmittance characteristics of the R filter 34A1, the G filter 34A2, and the B filter 34A3 for normal-light imaging mode and FIG. 27 shows an example of transmittance characteristics of the E1 filter 34A4, the G1 filter 34A5, and the R1 filter 34A6 for special-light imaging mode. For example, center wave length of the E1 filter 34A4 shown in FIG. 27 is 420 nm, center wave length of the G1 filter 34A5 is 540 nm, and center wave length of the R1 filter 34A6 is 630 nm.

By operating a movement motor 38 of the filter wheel unit 33D, it is possible to position the RGB filters 34A1 to 34A3 for normal imaging mode on the optical path and thereby activate the normal-light imaging mode (also referred to as "normal mode"), or position the filters 34A4 to 34A6 for special-light imaging mode on the optical path and thereby activate the special-light imaging mode.

The special-light imaging mode is roughly divided into auto fluorescence imaging mode and narrow band imaging mode.

In the auto fluorescence imaging (hereinafter also referred to as "AFI") mode, for example, a site to be observed is irradiated with blue excitation light needed to observe auto fluorescence of fluorescent substances such as collagen and with green light absorbed by blood hemoglobin. During shooting, a wave length component of the excitation light is cut off by the cut-off filter 28. Thus, the AFI mode displays a neoplastic lesion and a normal mucosa in an identifiable color tone on an endoscopic image and thereby supports early detection of a very small lesion such as cancer.

Conventional auto fluorescence imaging uses the property of auto fluorescence which becomes weaker upon irradiation with blue excitation light in tumor tissue than in normal tissue, where the auto fluorescence is fluorescence emitted by fluorescent substances such as collagen in a mucosa. However, regarding weakening of auto fluorescence, light is absorbed by blood hemoglobin as well as absorbed or scattered by thickened mucosal epithelium of tumor tissue. Thus, an inflammatory lesion, which can also cause attenuation of auto fluorescence, might be determined to be a tumor if irradiation with blue excitation light is solely relied upon.

In contrast, in the AFI mode, green reflected light, which is affected only by changes in hemoglobin without being affected by thickening of a mucosa, is combined with the blue excitation light. Consequently, normal tissue, tumor tissue, and deep blood vessels are observed to be light green, magentish, and dark-greenish, respectively, and thus become easier to distinguish.

On the other hand, the narrow band imaging (hereinafter also referred to as "NBI") mode is provided with imaging capabilities which have been improved through adjustment of spectral transmittance characteristics of irradiating light. For example, light with a short wave length such as blue light has a small penetration depth in a living body while light with a long wave length such as red light has a large penetration depth in a living body. Consequently, if short-wave narrow-band light is used in the NBI mode, the short-wave length light is reflected, carrying only information obtained near a surface of an observed site. This makes it possible to obtain observation images specialized in the surface of the observed site. That is, contrast of fine structures on the surface of the observed site is improved, and consequently fine patterns of, for example, capillary vessels can be shown clearly. Conversely, long-wave length light such as red is used in the NBI mode, the long-wave light is reflected, carrying information about a deep part of the observed site. This makes it possible to create images of the situation in the deep part of the observed site.

Also, the NBI mode allows capillary vessels in the mucosal epithelium as well as fine mucosal patterns to be highlighted through irradiation with two beams of narrow-band wave lengths easily absorbed by blood hemoglobin. In order to observe blood vessels with high contrast, by focusing on the use of light which combines the properties of being absorbed strongly in blood and being reflected and scattered intensely by the mucosal epithelium, the NBI mode irradiates the observed site with blue narrow-band light (e.g., 390 nm to 445 nm) for use to observe capillary vessels in the mucosal epithelium and green narrow-band light (e.g., 530 nm to 550 nm) for use to enhance contrast between thick blood vessels in deep part and the capillary vessels in the mucosal epithelium. The NBI mode can be used as an alternative method to dye spraying widely practiced for detailed diagnosis of an esophagus region and observation of pit patterns (ductal structures) in the large intestine, and is expected to help improve efficiency of examinations through reduction of examination time and unnecessary biopsies.

Illuminating light guided to the distal end portion 22 by the light guide fiber 25 is spread after passing through the illumination lens 24 mounted in an illuminating window (not shown) and is directed at a site to be observed in a body. Incidentally, a lamp identification unit 32 is disposed in the light source device 3D, where the lamp identification unit 32 is light source identification means for identifying the type of the light source device 3D. Information about the type of the lamp 30 (e.g., xenon lamp, halogen lamp, metal halide lamp, or light-emitting diode) is transmitted from the lamp identification unit 32 to the processing condition selection unit 13 via the control unit 11D.

The type of illuminating light, in other words, the imaging mode, is set by the surgeon via the input unit 6 or the like. The control unit 11D of the processor 4D controls the cut-off filter 28, the filter wheel unit 33D, and the like of the endoscope 2D based on the set imaging mode.

Figure 28:
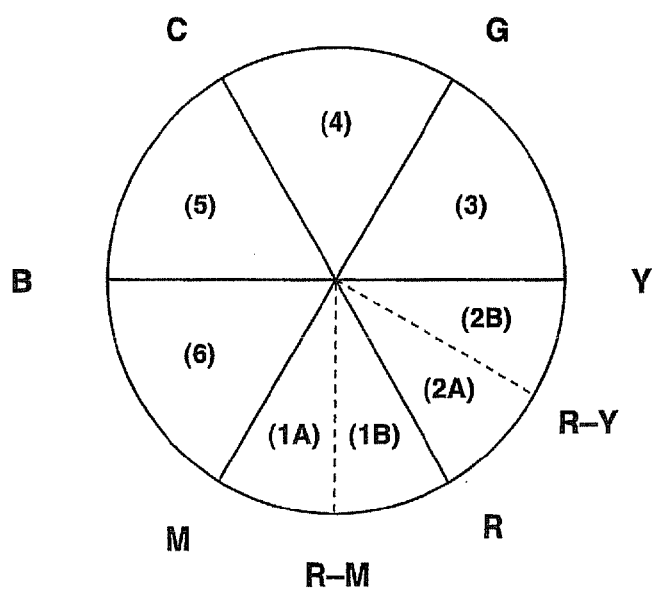
FIG. 28 is an explanatory diagram for illustrating 8-axis color correction performed on the endoscope system according to the fourth embodiment.
Figures 29, 30:
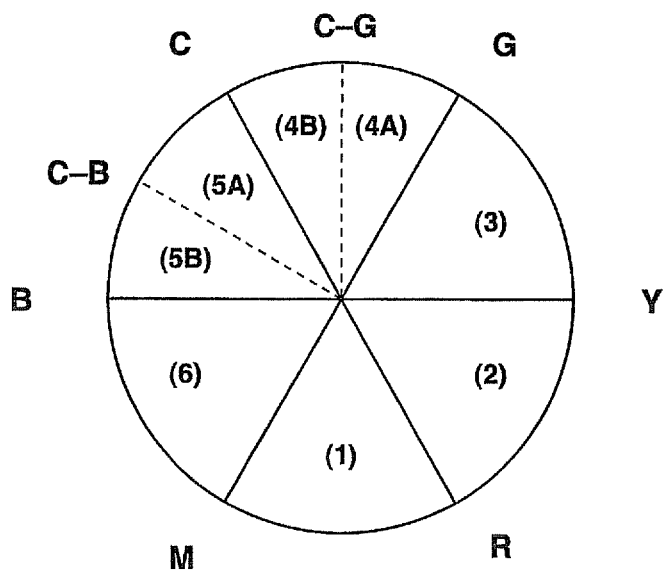
FIG. 29 is an explanatory diagram for illustrating 8-axis color correction performed on the endoscope system according to the fourth embodiment.
FIG. 30 is an explanatory diagram for illustrating 8-axis color correction performed on the endoscope system according to the fourth embodiment.

On the other hand, FIGS. 28 and 29 show the color space for a so-called 8-axis color correction process of the endoscope system 1D with two reference color axes established in addition to the six reference color axes. As shown in FIG. 28, with the endoscope system 1D, in the normal-light imaging mode, an R-Y color axis and an R-M color axis are established, respectively, between an R reference color axis and a Y reference color axis and between an R reference color axis and an M reference color axis based on the processing condition selected by the processing condition selection unit 13. Consequently, in the 8-axis color correction process, eight hue regions (1A), (1B), (2A), (2B), (3), (4), (5), and (6) are divided by the color axes.

If, for example, a correction coefficient is changed during the correction process of the R-M color axis, the region (1A) and the region (1B) on both sides of the R-M color axis are affected. Therefore, for example, when pixels belonging to the region (1B) are color corrected with respect to each hue region, three hue regions—not only the region (1B), but also the region (1A) and the region (2A)—are affected, but the region (1A) and the region (2A) are affected less, and the remaining regions are not affected.

However, in the special-light imaging mode, unlike in the normal-light imaging mode, the endoscopic images shot by the CCD 20 often have a subtle color tone centering around C color. Therefore, as shown in FIG. 29, with the endoscope system 1D, in the special-light imaging mode, a C-G color axis and a C-B color axis—one reference color axis each— are established between the C reference color axis and the G reference color axis and between the B reference color axis and the C reference color axis, based on the processing condition selected by the processing condition selection unit 13. Consequently, in the 8-axis color correction process, eight hue regions (1), (1), (2), (2), (3), (4A), (4B), (5A), (5B), and (6) are divided by the color axes.

As shown in FIGS. 30 and 31, it is determined in which of the eight hue regions a pixel color signal of an endoscopic image is located, based on magnitude relationship among an R signal, a G signal, and a B signal, and the hue region thus determined is color corrected. Being designed as an endoscopic image processing apparatus which performs a color correction process based on eight axes including two reference color axes established in advance, the endoscope system 1D lends itself to easy equipment design and minimizes complexity of circuits and the like.

Figure 32:
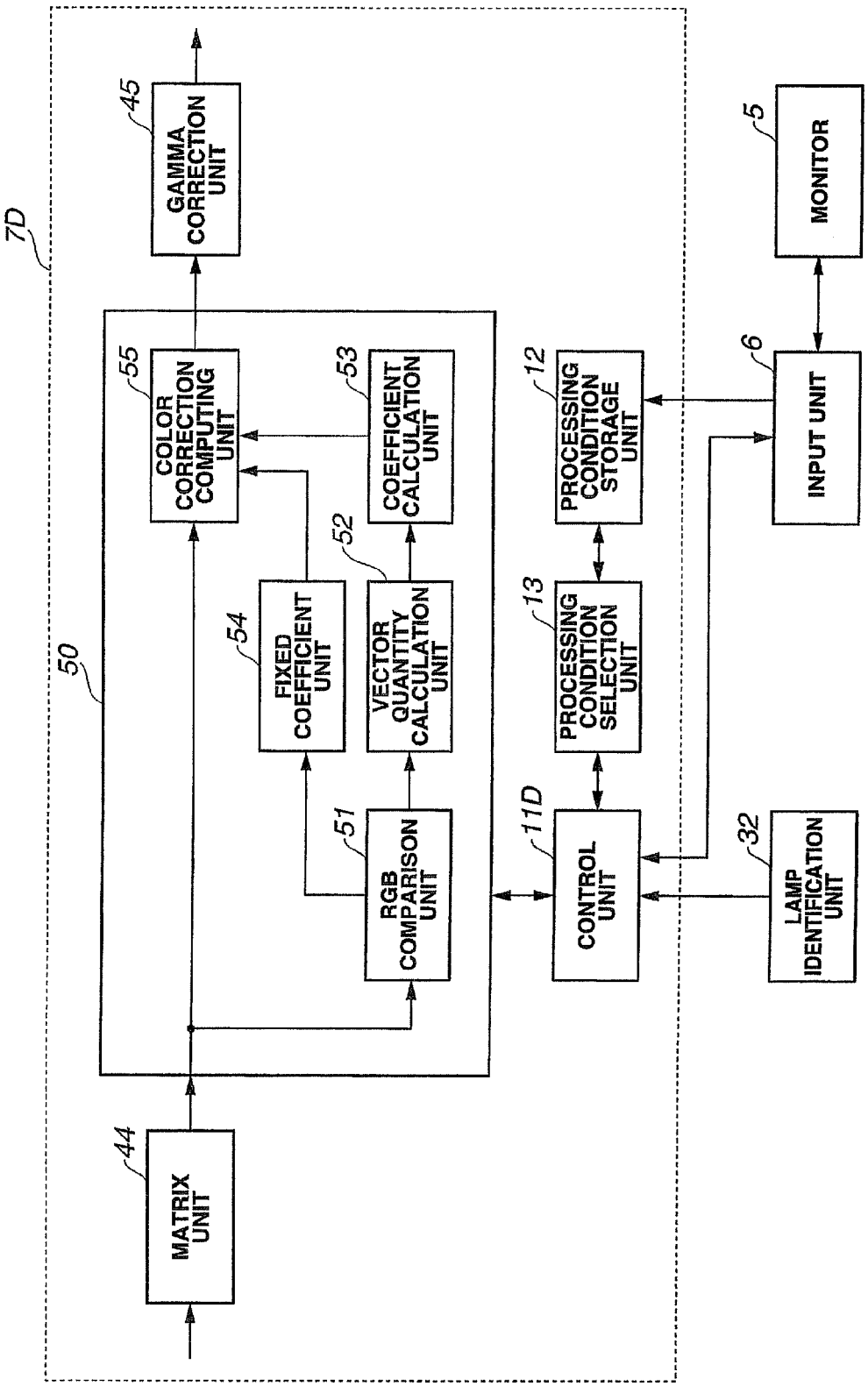
FIG. 32 is a block diagram for illustrating a color correction process performed by a color correction processing unit of the endoscopic image processing apparatus according to the fourth embodiment.

Next, the color correction process performed by the color correction processing unit 50 of the endoscopic image processing apparatus 7D according to the present embodiment will be described with reference to FIG. 32. The endoscopic image inputted into the color correction processing unit 50 from the matrix unit 44 is made up of a color signal which in turn is made up of an R signal, a G signal, and a B signal. As shown in FIGS. 30 and 31, the RGB comparison unit 51 determines in which of the eight hue regions the color signal of each pixel making up the endoscopic image is located, based on magnitude relationship among the R signal, the G signal, and the B signal depending on the current imaging mode.

In order to perform a color correction process with respect to each of the eight hue regions, the processing condition storage unit 12 prestores processing conditions each of which is made up of eight saturation (chroma) correction coefficients KRsat, KGsat, KBsat, KYsat, KCsat, KMsat, KRYsat, and KRMsat as well as eight hue correction coefficients KRhue, KGhue, KBhue, KYhue, KChue, KMhue, KRYhue, and KRMhue, for use in the normal-light imaging mode. The subscript following the symbol "K" which represents the correction coefficients is an abbreviation of hue. Also, RM represents an intermediate color between R and M while RY represents an intermediate color between R and Y.

For use in the special-light imaging mode, the processing condition storage unit 12 prestores processing conditions made up of eight saturation (chroma) correction coefficients KRsat, KGsat, KBsat, KYsat, KCsat, KMsat, KCGsat, and KCBsat as well as eight hue correction coefficients KRhue, KGhue, KBhue, KYhue, KChue, KMhue, KCGhue, and KCBhue, CG represents an intermediate color between C and G while CB represents an intermediate color between C and B.

Examples of processing conditions for specific imaging modes are shown in FIGS. 33A, 33B, and 33C where the processing conditions are stored in the processing condition storage unit 12. FIG. 33A shows a processing condition for normal-light imaging mode, FIG. 33B shows a processing condition for auto fluorescence imaging (AFI) mode, and FIG. 33C shows a processing condition for narrow band imaging (NBI) mode. The correction coefficients are expressed in relative values represented, for example, by integers between −100 and 100.

In the case of the color correction processing condition for normal-light imaging mode shown in FIG. 33A, one reference color axis each is established between the R reference color axis and the Y reference color axis and between the R reference color axis and the M reference color axis, and correction coefficients are set for each axis. On the other hand, in the case of the color correction processing conditions for special-light imaging mode shown in FIGS. 33B and 33C, one reference color axis each is established between the C reference color axis and the G reference color axis and between the B reference color axis and the C reference color axis, and correction coefficients are set for each color axis.

In the color correction process of the endoscope system 1D, the processing condition selection unit 13 selects an optimal processing condition according to the imaging mode from the processing conditions stored in the processing condition storage unit 12. Furthermore, the processing condition selection unit 13 selects the processing condition based on the information received from the lamp identification unit 32 via the control unit 11D. For the endoscope system 1D, the processing conditions include setting conditions of the reference color axes additionally established for the reference color axes of six colors and setting conditions of correction coefficients. In the endoscope system 1D, at least two reference color axes are established additionally and at least eight reference color axes are established in total. Three or more reference color axes may be established additionally, but two axes are preferable from the viewpoint of processing time and the like.

Consequently, the endoscope system 1D makes it easy to appropriately set the correction conditions used by the image processing unit 10.

In the endoscope system 1D, the processing condition selection unit 13 may select processing conditions according to the type of endoscope 2D. The type of endoscope 2D does not mean a model or the like. Since there are differences in color characteristics even among products of the same model due to variations in manufacturing processes, each individual endoscope 2D constitutes a type. Especially with regard to color CCDs, there are large differences in characteristics even among products of the same model due to variations in manufacture of color filters. Therefore, preferably the processing condition selection unit 13 selects processing conditions for each endoscope. The processing condition selection unit 13 identifies the type of endoscope based, for example, on information from the scope identification unit 16 disposed in the endoscope 2D. In other words, in the endoscope system 1D, the scope identification unit 16 stores different processing conditions for each endoscope and the processing condition selection unit 13 selects different processing conditions for each endoscope. Examples of processing conditions for specific types of endoscope are shown in FIGS. 34A and 34B, where the processing conditions are stored in the processing condition storage unit 12. FIG. 34A shows a processing condition in normal-light imaging mode for endoscope A and FIG. 34B shows a processing condition in normal-light imaging mode for endoscope B.

Also, in the endoscope system 1D, the processing condition selection unit 13 may select processing conditions according to the site to be photographed, according to the scene corresponding to the conditions in the body to be photographed, or according to the surgeon.

Furthermore, in the endoscope system 1D, the processing condition selection unit 13 includes a processing condition correction unit which corrects the selected processing condition. That is, as shown in FIG. 35, a numeric value of a processing condition can be corrected via the input unit 6 by selecting a target location 5D of a predetermined value using a selection marker 5C while checking values displayed, for example, in the form of a table 5B on the display screen 5A of the monitor 5. The correction of the processing condition selected by the processing condition selection unit 13 enables delicate adjustments of the color tone according to circumstances. As the processing condition selection unit 13, the input unit 6 or the scope switch 15 can be used, for example. Similarly, the processing conditions to be stored in the processing condition storage unit 12 can be set using the input unit 6 or the like.

As described above, the endoscope system 1D makes it easy to appropriately set the correction conditions used by the image processing unit 10 even if the color tone of the endoscope images changes greatly as a result of imaging mode switching.

Incidentally, the processing condition storage unit 12 and the processing condition selection unit 13 are described above as being separate components, independent of the control unit 11D and the image processing unit 10, but may be implemented integrally with the control unit 11D or the image processing unit 10 using the same hardware as the control unit 11D or the image processing unit 10.

As described above, the endoscopic image processing apparatus 7 makes it easy to appropriately set the correction conditions used by the image processing unit 10.

Incidentally, the special-light imaging mode provides endoscopic images of characteristic color tones if various filters are used in combination or the like. Thus, although in the endoscope system described above, one reference color axis each is established between the C reference color axis and the G reference color axis and between the B reference color axis and the C reference color axis, the present invention is not limited thereto.

The present invention is not limited to the embodiments and variations described above, and various changes and alterations may be made without departing from the spirit and scope of the present invention.

What is claimed is:

1. An endoscope system comprising:
   an endoscope equipped with an insertion portion inserted into a body of a subject, and an image pickup unit disposed at a distal end portion of the insertion portion;

an illumination unit which, being detachably connected to the endoscope, illuminates an inside of the body of the subject;

an imaging mode input unit used to set an imaging mode of the endoscope to one of a normal-light mode and a special-light mode;

a processing condition selection unit which selects, based on the imaging mode, a processing condition for a color correction process of an endoscopic image picked up by the image pickup unit; and a processor detachably connected to the endoscope and equipped with an image processing unit which performs the color correction process, under the processing condition selected by the processing condition selection unit, with respect to each of eight hue regions partitioned by eight reference color axes which consist of six reference color axes of R (red), M (magenta), B (blue), C (cyan), G (green), and Y (yellow) in a color space comprising six hue regions partitioned by six reference hue color axes, and two reference color axes each established additionally in one of two hue regions in contact with one of the six reference color axes selected based on the imaging mode.

2. The endoscope system according to claim 1, wherein the processing condition selection unit identifies a type of the endoscope based on information from an endoscope type identification unit disposed in the endoscope and selects the processing condition based on the imaging mode and the identified type of the endoscope.

3. The endoscope system according to claim 1, wherein the processing condition selection unit identifies a type of the illumination unit and selects the processing condition based on the imaging mode and the identified type of the illumination unit.

4. The endoscope system according to claim 3, wherein the type of the illumination unit is a light source type, and the light source type is one of a xenon lamp, a halogen lamp, a metal halide lamp, and a light-emitting diode.

5. The endoscope system according to claim 1, further comprising a body site input unit used to select a site in the body to be shot by the image pickup unit, wherein
the processing condition selection unit selects the processing condition based on the imaging mode and the selected site.

6. The endoscope system according to claim 1, further comprising a scene input unit used to select a scene according to conditions in the body to be shot by the image pickup unit, wherein
the processing condition selection unit selects the processing condition based on the imaging mode and the selected scene.

7. The endoscope system according to claim 6, wherein the scene is one of a normal scene and a bleeding scene.

8. The endoscope system according to claim 1, further comprising a surgeon information input unit used to input surgeon information, wherein
the processing condition selection unit selects the processing condition based on the imaging mode and the inputted surgeon information.

9. The endoscope system according to claim 1, wherein:
when the imaging mode is the normal-light mode, the processing condition selected by the processing condition selection unit allows to establish one reference color axis between an R (red) reference color axis and a Y (yellow) reference color axis and one reference color axis between the R (red) reference color axis and an M (magenta) reference color axis; and
when the imaging mode is the special-light mode, the processing condition selected by the processing condition selection unit allows to establish one reference color axis between a C (cyan) reference color axis and a G (green) reference color axis and one reference color axis between a B (blue) reference color axis and the C (cyan) reference color axis.

10. The endoscope system according to claim 1, wherein the processing condition selection unit comprises a processing condition correction unit which corrects the selected processing condition.

11. The endoscope system according to claim 1, further comprising a display unit which has a graphics input capability of displaying an endoscopic image subjected to a color correction process and a color space image and allowing the processing condition to be set by moving a condition setting mark on the reference color axes of the color space image, wherein as the processing condition is set using the condition setting mark, a color tone of the endoscopic image displayed on the display unit changes in real time.

12. An endoscopic image processing apparatus comprising:
an imaging mode input unit used to set an imaging mode of an endoscope to one of a normal-light mode and a special-light mode;
processing condition selection means which selects a processing condition for a color correction process of an endoscopic image based on the imaging mode; and
image processing means which performs the color correction process, under the processing condition selected by the processing condition selection means, with respect to each of hue regions partitioned by eight reference color axes which consist of six reference color axes of R (red), M (magenta), B (blue), C (cyan), G (green), and Y (yellow) in a color space comprising six hue regions partitioned by the six reference color axes, and two reference color axes each established additionally in one of two hue regions in contact with one of the six reference color axes selected based on the imaging mode.

* * * * *